(12) United States Patent  
Crucilla

(10) Patent No.: US 8,529,462 B2  
(45) Date of Patent: Sep. 10, 2013

(54) APPARATUS AND METHOD FOR PASSIVE TESTING OF ALCOHOL AND DRUG ABUSE

(75) Inventor: Christopher Crucilla, Douglas, AZ (US)

(73) Assignee: Justice EZ Trac, LLC, Easton, CT (US)

( * ) Notice: Subject to any disclaimer, the term of this patent is extended or adjusted under 35 U.S.C. 154(b) by 582 days.

(21) Appl. No.: 12/658,349

(22) Filed: Feb. 5, 2010

(65) Prior Publication Data

US 2010/0204600 A1     Aug. 12, 2010

Related U.S. Application Data

(60) Provisional application No. 61/207,028, filed on Feb. 6, 2009.

(51) Int. Cl.
*A61B 5/08* (2006.01)
*G06F 21/00* (2013.01)

(52) U.S. Cl.
USPC .......................... 600/532; 600/529; 713/186

(58) Field of Classification Search
USPC ......... 600/529–543; 713/185–186; 340/576; 707/769, 803
See application file for complete search history.

(56) References Cited

U.S. PATENT DOCUMENTS

| | | | |
|---|---|---|---|
| 6,256,737 B1 * | 7/2001 | Bianco et al. | 713/186 |
| 2003/0023182 A1 * | 1/2003 | Mault et al. | 600/532 |
| 2003/0069753 A1 * | 4/2003 | Brown | 705/2 |
| 2004/0239510 A1 * | 12/2004 | Karsten | 340/576 |
| 2005/0065446 A1 * | 3/2005 | Talton | 600/529 |
| 2008/0243005 A1 * | 10/2008 | Jung et al. | 600/481 |

* cited by examiner

*Primary Examiner* — Patricia Mallari
*Assistant Examiner* — Tiffany Weston
(74) *Attorney, Agent, or Firm* — Knechtel, Demeur & Samlan

(57) ABSTRACT

An automated system and method for passive testing of alcohol and drug abuse. The system enters a participant or subject into the system who is to be monitored during a probationary or other program for alcohol or drug abuse offenders. The system provides a drug testing home device or a drug testing kiosk device for use by the participant. The system enrolls the biometrics information of the participant into the computer system (e.g., finger print, voice, image, volatile compound organic gas level, and pH level). When the participant is to be tested in accordance with a testing schedule, the system validates these same biometrics of the participant, conducts the test, and then analyzes the test information for determining if the participant has been using alcohol or other drugs and should be subjected to a confirming urinalysis exam.

33 Claims, 46 Drawing Sheets

Fig. 19

IntakeWorksheet — 382

| Question | | | 384 — 386 | | | | | |
|---|---|---|---|---|---|---|---|---|
| Do you wake up often during sleep? | ○ Yes | ○ No | | Do you snore? | ○ Light | ○ Moderate | ○ Heavy | |
| Does leg pain wake you at night? | ○ Yes | ○ No | | Do you take prescription medications: | | | | |
| Do you walk, run, bike, workout? | ○ Yes | ○ No | | Morning ○ Yes ○ No | | Evening ○ Yes ○ No | | |
| Do you have sleep apnea? | ○ Yes | ○ No | | Noon ○ Yes ○ No | | Bed Time ○ Yes ○ No | | |
| Do you work shift work/unusual hours? | ○ Yes | ○ No | | Are you taking prescription medications for: | | | | |
| Do you work with chemicals or products that contain alcohol? | ○ Yes | ○ No | | Pain ○ Yes ○ No | | ADHD ○ Yes ○ No | | |
| Do you use tobacco products? | ○ Yes | ○ No | | Anxiety ○ Yes ○ No | | Depression ○ Yes ○ No | | |

Rate your activity level at work:
  ○ Low   ○ Moderate   ○ High

Other condition ○ Yes ○ No  [Medications] — 388

Rate your activity level in general:
  ○ Low   ○ Moderate   ○ High

Describe your past alcohol and drug abuse:
  ○ Recreational
  ○ More than recreational, but not every day
  ○ More than three times a week
  ○ Every day Do you use energy supplements/drinks?
  ○ Never   ○ Low use   ○ Moderate use   ○ High use What is your job? [_____]

Note: Worksheet is not saved until 'Save Changes' is pressed.

[Cancel]                                                                [Done] — 412

Fig. 21

Subject Information

- 204 — SubjectID: Test0002
- 418 — OK
- 206 — First Name: A
- 208 — Last Name: Subject
- 210 — DOB:
- 212 — Job Classification: Client
- 214 — Other Classification:
- 220 — ☑ Has Fingerprint
- 222 — ☑ Has Voice
- 224 — ☑ Has Image
- 232 — ☑ Default Email
- 234 — ☑ Send BAC Fail Email
- 216 — Upload Schedule: Monday / Thursday
- 236 — Alternate Emails If no alternate email addresses are specified the default PassPoint email will be used.

Fig. 31

Pass Email

MobileBreath Test Results

Subject Name: Thorpe, Stan
Subject ID: 1971
Agency: Greene
MobileBreath Unit ID: STM550

Date of Test: Thu Jan, 28 2010
Time of test: 05:18PM

Verification Methods:
Fingerprint verified
Voice not verified
Image verified

Contamination Test - Passed

Type of test taken: Screening Brealthalyzer Test

Test Result: Negative

Note: No Evidence of Alcohol Use.

Images must be verified: <A href="http://www.sleeptime.us/verification.aspx?ID=290">http://www.sleeptime.us/verification.aspx?ID=290</A>

Fig. 32

Failed Email

MobileBreath Test Results

Subject Name: Thorpe, Stan
Subject ID: 1971
Agency: Greene
MobileBreath Unit ID: STM550

Date of Test: Tue Jan, 26 2010
Time of test: 09:02PM

Verification Methods:
Fingerprint verified
Voice not verified
Image verified

Contamination Test - Passed

Type of test taken: Evidentiary Breathalyzer Test

BAC: 0.0

Test Result: Negative

Note: No Evidence of Alcohol Use.

Images must be verified: <A href="http://www.sleeptime.us/verification.aspx?ID=284">http://www.sleeptime.us/verification.aspx?ID=284</A>

Fig. 33

Test Not Taken Email

MobileBreath Test Results

Subject Name: York, Anne
Subject ID: POLITAL
Agency: Greene
MobileBreath Unit ID: STM550

Date of Test: Mon Jan, 18 2010
Time of test: 05:05PM

Verification Methods:
Fingerprint not verified
Voice not verified
Image Not Captured: Face not in correct position Contamination Test - Not Run Type of test taken: Screening Brealthalyzer Test Test Result: Incomplete Note: Subject did not complete this breathalyzer test.

Note: Inform subject MobileBreath indicates possible alcohol use.

Images cannot be verified.

Fig. 34

Test Incomplete - Fault Email

MobileBreath Test Results

Subject Name: josh111, josh111
Subject ID: test111
Agency: Greene
MobileBreath Unit ID: STM560

Date of Test: Thu Jan, 28 2010
Time of test: 04:58PM

Verification Methods:
Fingerprint verified
Voice verified
Image verified

Contamination Test - Not Run

Type of test taken: Screening Brealthalyzer Test

Test Result: Incomplete

Note: Subject did not complete this breathalyzer test.

Note: Inform subject MobileBreath indicates possible alcohol use.

Fig. 35

Validation Failed

MobileBreath Test Results

Subject Name: York, Anne
Subject ID: POLITAL
Agency: Greene
MobileBreath Unit ID: STM550

Date of Test: Mon Jan, 18 2010
Time of test: 07:48PM

Verification Methods:
Fingerprint not verified
Voice not verified
Image is not an exact match.

Contamination Test - Passed

Type of test taken: Screening Brealthalyzer Test

Test Result: Negative

Note: No Evidence of Alcohol Use.

Images must be verified: <A href="http://www.sleeptime.us/verification.aspx?ID=279">http://www.sleeptime.us/verification.aspx?ID=279</A>

Fig. 36

Evidentiary Email

MobileBreath Test Results

Subject Name: Thorpe, Stan
Subject ID: 1971
Agency: Greene
MobileBreath Unit ID: STM550

Date of Test: Tue Jan, 26 2010
Time of test: 08:42PM

Verification Methods:
Fingerprint verified
Voice verified
Image verified

Contamination Test - Passed

Type of test taken: Screening Brealthalyzer Test

Test Result: Positive

Note: Client shows evidence of alcohol and has been instructed to wait 15 minutes and take an Evidentiary test.

Fig. 37

Missed Test Email

MobileBreath Test Results

Subject Name: Thorpe, Stan
Subject ID: 1971
Agency: Greene
MobileBreath Unit ID: STM550

Dates and Times of missed tests since the last time MobileBreath was turned on.
Tue Jan, 26 2010 08:58PM - Thu Jan, 28 2010 11:02AM Wednesday - 10:00AM - 1:00PM

Fig. 38

Missed BACs Report

Greene
24 Hour Missed BAC Tests for Tue Jan, 26 2010 8:00AM

Officer:--Not Assigned--

Officer:McGraw, Quickdraw POID:
1234577
Subject Thorpe, Stan (1971)
Tue Jan, 26 2010 04:55PM - Wed, 27 2010 12:00AM
| Day | Time |
| --- | --- |
| Tuesday | 6:00PM |
| Tuesday | 8:43PM |

Fig. 39

Validation Requests

Greene
MovieBreath Validation Requests As Of February 01, 2010

| Last Name | First Name | SubjectID | Date | Validate ID |
|---|---|---|---|---|
| test1 | chris | 555 | 07/28/2009 01:02AM | 55 |
| test1 | chris | 555 | 08/04/200 908:19PM | 56 |
| test1 | chris | 555 | 08/14/2009 06:51PM | 58 |
| test1 | chris | 555 | 08/14/2009 08:15PM | 59 |
| test1 | chris | 555 | 08/14/2009 08:31PM | 60 |
| test1 | chris | 555 | 08/14/2009 08:33PM | 61 |
| test1 | chris | 555 | 08/14/2009 08:35PM | 62 |
| test1 | chris | 555 | 08/14/2009 10:15PM | 63 |
| test1 | chris | 555 | 08/14/2009 10:19PM | 64 |
| test1 | chris | 555 | 08/15/2009 11:19PM | 71 |
| test1 | chris | 555 | 08/16/2009 01:17AM | 72 |
| crucilla | josh | angles40 | 08/26/2009 01:22PM | 95 |
| crucilla | josh | angles40 | 08/26/2009 01:38PM | 96 |

Fig. 40

BAC Activity Report

Polital

MobileBreath BAC Activity Report for Fri Jan, 01 2010 - Mon Feb, 01 2010

Officer:--Not Assigned --

Subject York, Annemarie (Anne)

| Date | Type | Reason | Result | BAC |
|---|---|---|---|---|
| Sat 01/02/10 06:53:PM | Evidentiary | Missed Screening Blow Test(s) | Pass | 0.0 |
| Sat 01/02/10 09:46PM | Screening Blow | Scheduled | Pass | |
| Sun 01/03/10 01:02PM | Screening Blow | Scheduled | Pass | |
| Sun 01/03/10 10:00PM | Screening Blow | Scheduled | Pass | |
| Mon 01/04/10 12:45PM | Screening Blow | Scheduled | Pass | |
| Mon 01/04/10 10:01PM | Screening Blow | Scheduled | Pass | |
| Tue 01/05/10 01:15PM | Screening Blow | Scheduled | Fault | |
| Thu 01/07/10 02:48PM | Evidentiary | Missed Screening Blow Test(s) | Pass | 0.0 |
| Thu 01/07/10 03:20PM | Screening Blow | Scheduled | Pass | |

Fig. 41

Passive Pass

PassPoint Analysis for Subject York, Nick(Sykron)     Agency Polital

Identity Verified by Finger Scan, Verified by Voice, verified by Image

Device 100   Scanned: Mon   Analyzed: Mon
                Feb, 01 2010    Feb, 01 2010
                11:53AM         11:54AM

Passive Breathalyzer Test.

BAC:NEG
No Evidence of Alcohol Use.

Images must be verified:
http://www.sleeptime.us/verification.aspx?ID=292

Receipt

Agency: Polital
Name: York, Nick
ID #: Sykon
Date/Time:2/1/2010 11:53AM

Officer: York POID:PO002
BAC:NEG
Conclusion: No Evidence of Alcohol

Fig. 42

Passive Fail

PassPoint Analysis for Subject York, Nick(Sykron)     Agency Polital

Identity Verified by Finger Scan, Verified by Voice, Verified by Image

Device 100   Scanned: Mon Feb, 01 2010     Analyzed: Mon Feb, 01 2010
                11:55AM                    11:55AM

Passive Breathalyzer Test.

BAC: POS
The suggested substances to test for include: ALC
Client shows evidence of alcohol and has been instructed to wait 15 minutes and test again.

Images must be verified:
http://www.sleeptime.us/verification.aspx?ID=293

Receipt

Agency: Polital
Name: York, Nick
ID #: Sykon
Date/Time:2/1/2010 11:55AM

Officer: York POID:PO002
BAC:POS
Conclusion: Test again in 15 minutes
Message: This is a test

APPARATUS AND METHOD FOR PASSIVE TESTING OF ALCOHOL AND DRUG ABUSE

I. CROSS-REFERENCE TO RELATED APPLICATION

This patent application is a non-provisional application claiming priority from U.S. Provisional Patent Application Ser. No. 61/207,028, entitled Apparatus and Method For Passive Testing of Alcohol and Drug Abuse, filed on Feb. 6, 2009, and is fully incorporated herein by reference.

II. FIELD OF THE INVENTION

The present invention relates to alcohol and drug testing and, more particularly, to a unique automated system and method for determining if alcohol and/or drug testing is necessary for individuals at risk for or recovering from alcohol and/or drug abuse.

III. DESCRIPTION OF THE PRIOR ART

When an individual is conditionally released from their Court ordered confinement or arrested for driving while under the influence of alcohol, driving while inebriated, for possession and use of marijuana or other narcotic or substance, the fate of the individual rests with the court system. In almost all instances, when the individual returns to society, that individual is subjected to a probationary period. For example, an individual released from prison on parole is referred to as a "parolee"; an individual released from jail on probation is referred to as a "probationer"; and an individual released from Court supervision on drug related crimes is referred to as a "drug court participant."

During this probationary period, the individual is required to undergo mandatory review and alcohol and/or drug testing to confirm the individual's compliance with their probation. As part of the mandatory review and testing, one means available in the past has been to have the individual, at prearranged or other scheduled times, be subjected to at least bi-weekly urinalysis exams. Each urinalysis exam consisting of the individual creating a urinalysis sample while being watched by a witness such as their probation officer or other assigned personnel.

Although this system works, there are some inherent problems for the majority of individuals who comply with their probation by not abusing alcohol and not taking or using illegal or prohibited drugs. First, performing the urinalysis exam while being watched by another person is invasive and humiliating for the individual and, at the very least, uncomfortable for the witness. Second, if the individual is complying with their probation, a routine bi-weekly urinalysis exam to confirm the non-use of alcohol or drugs becomes costly due to all the time and expense invested in the personnel required to conduct each exam and all the personnel required to analyze each exam.

To solve this problem, the Applicant has invented an automated system and method for determining if an individual is potentially still engaging in alcohol and/or drug abuse and, therefore, should be subjected to a urinalysis exam to confirm the results and/or compliance with their probation or monitoring program. If Applicant's invention determines that the individual is not a person that should be subjected to a urinalysis exam because the individual does not appear to be engaging in alcohol or drug abuse, this: (a) reduces the invasion and humiliation routinely experienced by the individuals complying with their probation or monitoring program, (b) reduces the discomfort that may be experienced by the probation officer or other witness involved in the urinalysis exam, and (c) reduces the number of urinalysis exams conducted which transcends into reduced cost savings that may be expended toward other necessary matters.

Thus, there is a need and there has never been disclosed Applicant's unique automated system and method for passive testing of alcohol and drug abuse.

IV. SUMMARY OF THE INVENTION

The present invention is an automated system and method for passive testing of alcohol and drug abuse. The system enters a participant or subject into the system who is to be monitored during a probationary or other program for alcohol or drug abuse offenders. The system provides a drug testing home device or a drug testing kiosk device for use by the participant. The system enrolls the biometrics information of the participant into the computer system (e.g., finger print, voice, image, volatile compound organic gas level, and pH level). When the participant is to be tested in accordance with a testing schedule, the system validates these same biometrics of the participant, conducts the test, and then analyzes the test information for determining if the participant has been using alcohol or other drugs and should be subjected to a confirming urinalysis exam.

V. BRIEF DESCRIPTION OF THE DRAWINGS

The Description of the Preferred Embodiment will be better understood with reference to the following figures:

FIG. 19 is a diagram of the intake worksheet pane resulting from the selection of the intake worksheet button from the add new subject pane to begin entering the history and medications of the participant.

FIG. 21 is a diagram of the subject information pane resulting from the selection of the add subject button from the add new subject pane to complete the enrollment of the participant into the system.

FIG. 31 is a diagram of the pass email that may be sent to all the interested persons in notification of a test result from the testing process for the participant using the drug testing home device.

FIG. 32 is a diagram of the failed email that may be sent to all the interested persons in notification of a test result from the testing process for the participant using the drug testing home device.

FIG. 33 is a diagram of the test not taken email that may be sent to all the interested persons in notification of a test result from the testing process for the participant using the drug testing home device.

FIG. 34 is a diagram of the test incomplete—fault email that may be sent to all the interested persons in notification of a test result from the testing process for the participant using the drug testing home device.

FIG. 35 is a diagram of the validation failed email that may be sent to all the interested persons in notification of a test result from the testing process for the participant using the drug testing home device.

FIG. 36 is a diagram of the evidentiary email that may be sent to all the interested persons in notification of a test result from the testing process for the participant using the drug testing home device.

FIG. 37 is a diagram of the missed test email that may be sent to all the interested persons in notification of a test result from the testing process for the participant using the drug testing home device.

FIG. 38 is a diagram of the missed bac report email that may be sent to all the interested persons in notification of a test result from the testing process for the participant using the drug testing home device or drug testing kiosk device.

FIG. 39 is a diagram of the validation requests email that may be sent to all the interested persons in notification of a test result from the testing process for the participant using the drug testing home device or drug testing kiosk device.

FIG. 40 is a diagram of the bac activity report email that may be sent to all the interested persons in notification of a test result from the testing process for the participant using the drug testing home device or drug testing kiosk device.

FIG. 41 is a diagram of the passive pass email that may be sent to all the interested persons in notification of a test result from the testing process for the participant using the drug testing kiosk device.

FIG. 42 is a diagram of the passive fail email that may be sent to all the interested persons in notification of a test result from the testing process for the participant using the drug testing kiosk device.

VI. DETAILED DESCRIPTION OF THE PREFERRED EMBODIMENT

The individuals participating in this alcohol and drug abuse monitoring system through a probationary period or other agency program are referred to herein as participants. Applicant's invention is used, during this period, to detect if the participant has engaged in recent episodes of alcohol or other drug abuse. The invention analyzes the air of the breath of the participants to determine if the gases and/or acidity data or information obtained from the air of the breath are consistent with alcohol or other drug abuse and, if so, provides the results to the participant and/or agency to further request that the participant complete a urine toxicology test for confirming evidence of the participant's consumption of alcohol or other drugs.

Figure 1:
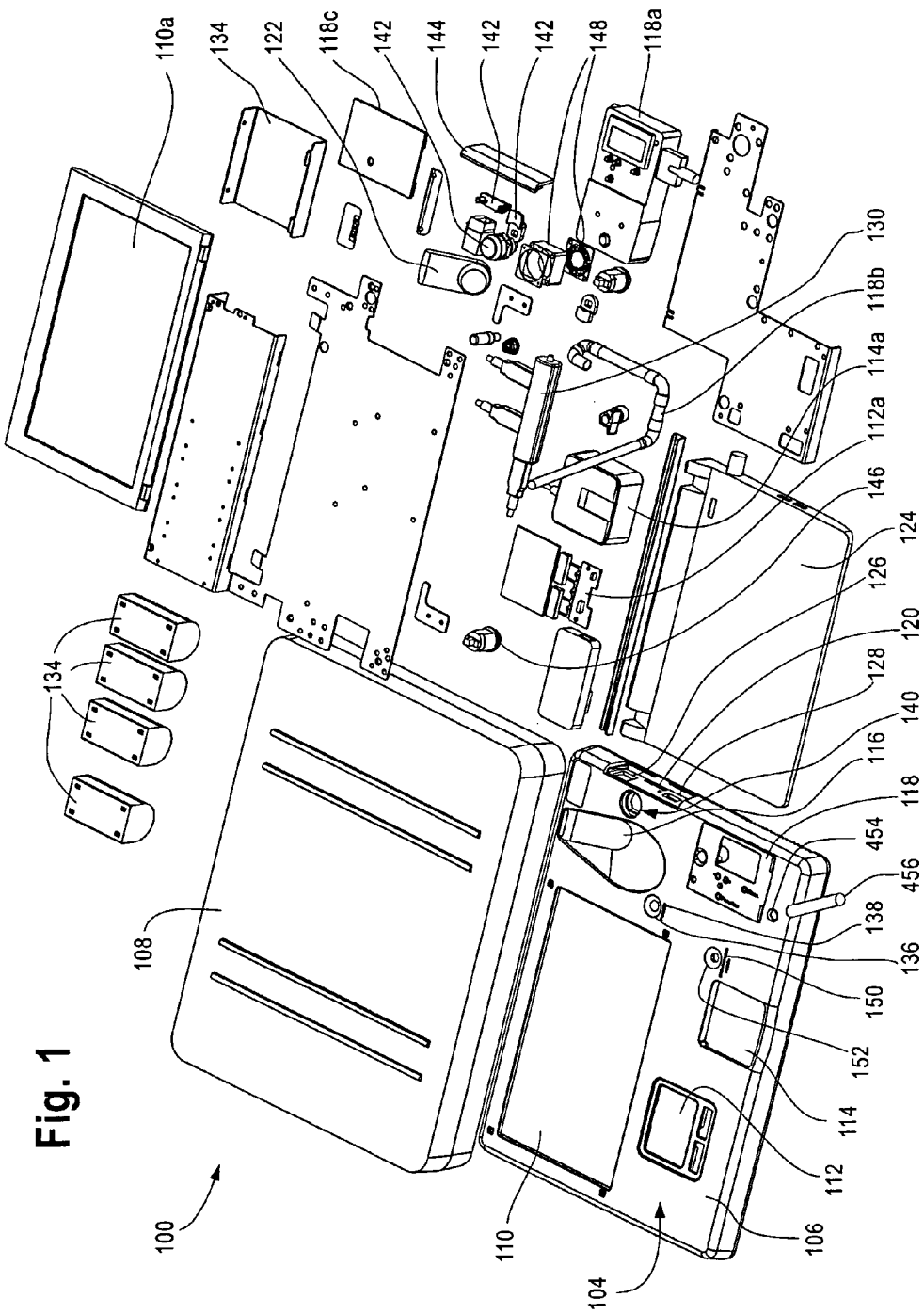
FIG. 1 is an exploded diagram illustrating the computer hardware used in Applicant's system and, in particular, illustrating a drug testing home device and associated components.
Figure 2:
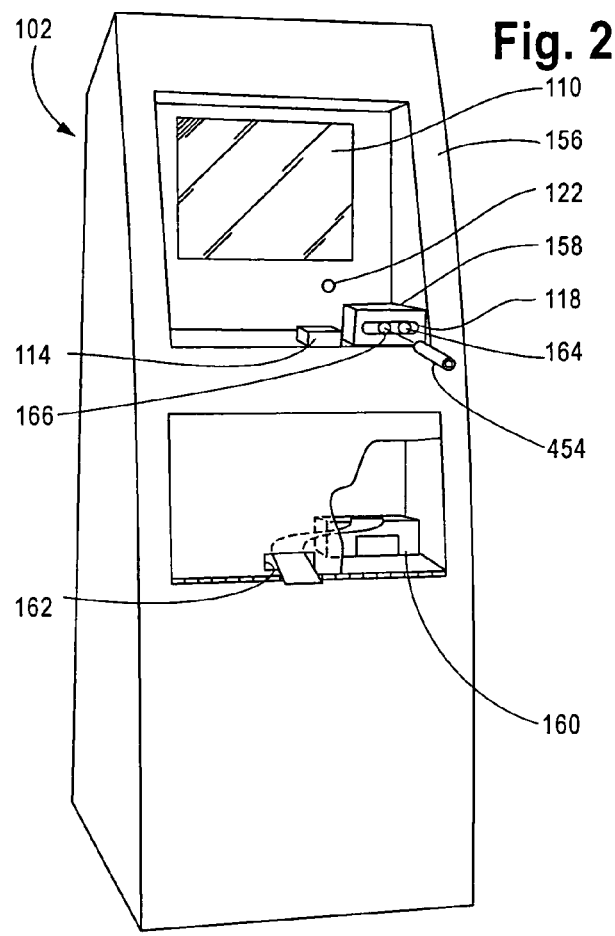
FIG. 2 is a diagram illustrating an alternate embodiment of the computer hardware used in Applicant's system and, in particular, illustrating the front perspective view of a drug testing kiosk device and associated components.
Figure 3:
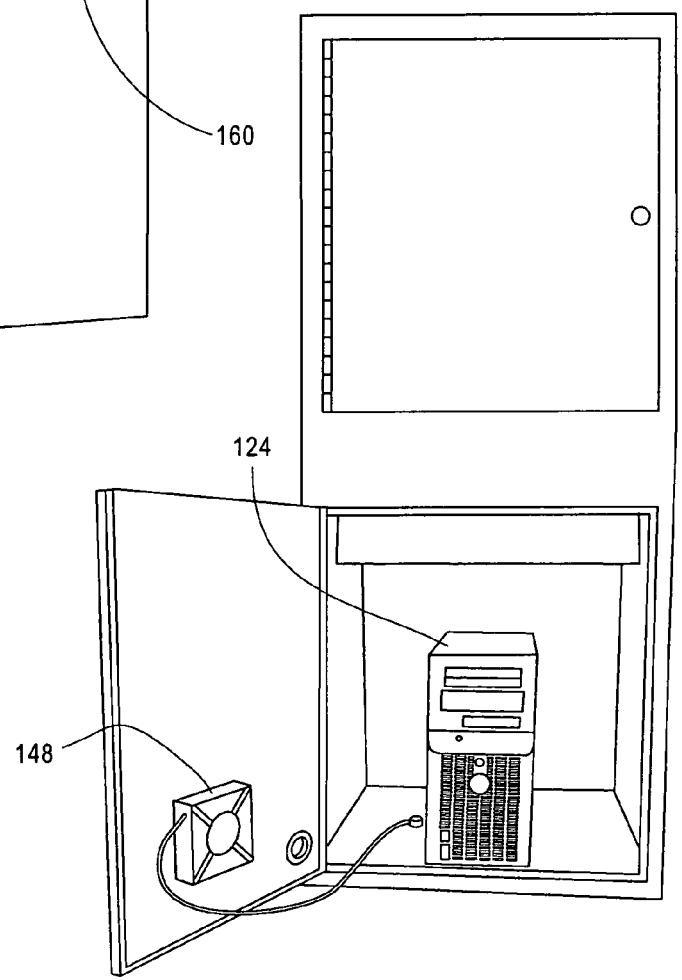
FIG. 3 is a diagram illustrating the alternate embodiment of the computer hardware used in Applicant's system and, in particular, illustrating the back view of the drug testing kiosk device and associated components.

Applicant's invention consists of the interaction between computer hardware and computer software. The computer hardware consists of a drug testing home device 100, as illustrated in FIG. 1; or alternatively a drug testing kiosk device 102, as illustrated in FIGS. 2 and 3. Although each reference to these devices 100 and 102 refers to "drug testing," each of these devices, as described herein, are also used for alcohol testing.

Referring to FIG. 1, the drug testing home device 100 is illustrated. The drug testing home device 100 is designed for use by the participants in the privacy of their home or residence or as a self-contained device that may travel with and/or be used by the participant to comply with the participant's testing schedule, described in further detail below, in any desired or convenient location.

The drug testing home device 100 comprises a housing 104 having a base 106 and a cover 108. Contained within the base 106 of the housing 104 is a liquid crystal display screen 110, a touch pad 112, a finger print reader 114, a recess 116 for a camera, a breathalyzer or multi-testing device 118, external ports 120, and a central processing unit computer 124.

The housing 104 is used as the protective casing for the drug testing home device 100. In the preferred embodiment, the housing 104 is preferably a heavy duty 1090 Pelican case manufactured by Pelican Products, Inc. located in California. Alternatively, any other housing 104 known to one skilled in the art may be used provided that it is used as the carrying and protective case for the drug testing home device 100 as described herein.

The liquid crystal display screen 110 is a thin, flat panel used for electronically displaying information such as text, images, and other information on the drug testing home device 100. In the exploded diagram, the further components of the liquid crystal display 110 are illustrated at 110a. In the preferred embodiment, the liquid crystal display 110 is preferably part of the central processing unit computer 124 manufactured by Acer, Inc. located in San Jose, Calif. Alternatively, any other liquid crystal display screen 110 known to one skilled in the art may be used provided that it is used to electronically display the information on the drug testing home device 100 as described herein.

The touch pad 112 is a stationary pointing device that provides a small, flat surface for the participant to slide a finger over using the same movements as one would a mouse to operate the computer system described in further detail below. In the exploded diagram, the further components of the touch pad 112 are illustrated at 112a. In the preferred embodiment, the touch pad 112 is preferably an ATP-400PB Adesso 2 button touch pad manufactured by Adesso, Inc. located in Walnut, Calif. Alternatively, any other touch pad 112 known to one skilled in the art may be used provided that it is used to operate the computer system as described herein.

The finger print reader 114 is used to scan or read the finger print of a participant and generate a raw fingerprint image of the participant's finger. In the exploded diagram, the further components of the finger print reader 114 are illustrated at 114a. In the preferred embodiment, the finger print reader 114 is preferably a Futronic FS88 FIPS201/PIV Compliant USB2.0 Fingerprint Scanner manufactured by Futronic Technology Company Limited located in Hong Kong. Alternatively, any other finger print reader 114 known to one skilled in the art may be used provided that it is used or operated to read the finger prints of participants and generate fingerprint images of the participant for use as described herein.

Contained within the recess 116 is a camera 122 which is used to read and generate a facial image of the participant. In the preferred embodiment, the camera 122 is a Logitech Quick Cam Pro (autofocus) for notebooks manufactured by Logitech located in Fremont, Calif. Alternatively, any other camera 122 known to one skilled in the art may be used provided that it is used or operated to read and generate a facial image of the participant for use as described herein.

The breathalyzer device 118 is a breath alcohol testing device. In the exploded diagram, the further components of the breathalyzer 118 are illustrated at 118a, a tube 118b that connects to the breathalyzer 118a, and a breathalyzer door 118c to cover the breathalyzer device 118. In the preferred embodiment, the breathalyzer 118 is preferably a FC20 Lifeloc manufactured by Lifeloc Technologies, Inc. located in Wheat Ridge, Colo. Alternatively, any other breathalyzer device 118 known to one skilled in the art may be used provided that it is used to test the breath alcohol of the participant as described herein.

The breathalyzer device 118 is powered on and off using an on/off switch or power button 150 to toggle the breathalyzer 118 between being powered in the "on" and/or powered in the "off" position. When the power button 150 is in the "on" position, the breathalyzer device 118 is ready for use. When the breathalyzer device 118 is energized, a power light display 152 will engage and display a color, such as red (or any other desired color known to one skilled in the art), to visually indicate that the breathalyzer device 118 is energized and ready for use.

Alternatively, as the breathalyzer device 118 is a breath alcohol testing device only, the breathalyzer device 118 may be replaced with a multi-testing device 118 that continues to test for breath alcohol (i.e., breathalyzer or ethanol sensor) but also tests for drugs using a volatile organic compound (i.e., voc) gas sensor and a pH sensor (i.e., for the acidity or basicity of the air of a breath). As illustrated in FIGS. 43(A)-(F), the electrical schematic or circuit board diagram of the multi-testing device 118 continues to provide the breathalyzer or ethanol sensor 540 and then further includes the Volatile Organic Compound (VOC) sensor 542 and the pH sensor 544 and the connection of each of these sensors to the computer 546. Extra circuits 548 and 550 are also included, if desired. In this manner, as described in further detail below, during a single test (i.e., blow from the participant into the multi-testing device 118), the breathalyzer or ethanol sensor 540 can test for the presence of alcohol and the Volatile Organic Compound (VOC) sensor 542 and the pH sensor 544 can test for the presence of drugs.

The external ports 120 affords a simple technique for interfacing with external circuitry for the drug testing home device 100. In the preferred embodiment, the external ports 120 of the drug testing home device 100 comprises an ethernet port 126 and an extra USB port 128. Should more than one extra USB port 128 be desired, a USB port hub 130 may be inserted into the USB port 128 to increase the number of USB ports available to the drug testing home device 100. Alternatively, the external ports 120 may comprise any other computer device ports desired for use as described herein.

The central processing unit computer 124 is the computer system that carries out the instructions of the computer software. In the preferred embodiment, the central processing unit computer 124 is preferably an Accer Aspire one D250-1165 Computer Model KAV60 manufactured by Accer, Inc. located in San Jose, Calif. Alternatively, any other central processing unit computer 124 known to one skilled in the art may be used provided that it is used and operated as described herein.

The central processing unit computer 124 utilizes a modem 154 to communicate via the interne or world wide web. In the preferred embodiment, the modem 154 is a GPRS Modem AT&T Sierra Mercury 885 manufactured by AT&T Inc. located in San Antonio, Tex. Alternatively, any other modem 154 known to one skilled in the art may be used provided that it is used and operated as described herein.

The drug testing home device 100 is powered by a plurality of batteries 132 (also referred to herein as the "power source") releaseably contained within a battery box 134. In the preferred embodiment, the battery is a NiMH 7.2 volt battery. Alternatively, any other type of battery 132 known to one skilled in the art may be used or, an AC adaptor or other means may be used, provided that it provides sufficient electrical power or flow of electricity to power the device 100.

The drug testing home device 100 is powered on and off using an on/off switch or power button 136 to toggle the drug testing home device 100 between being powered in the "on" and/or powered in the "off" position. In the exploded diagram, the further components of the power button 136 are illustrated at 136a. When the power button 136 is in the "on" position, the power source 132 will generate a flow of electricity to energize the drug testing home device 100 for use. When the drug testing home device 100 is energized, a power light display 138 will engage and display a color, such as red (or any other desired color known to one skilled in the art), to visually indicate that the drug testing home device 100 is energized by the power source 132 and ready for use.

A locking means 140 is also provided as security to lock the drug testing home device 100. In the exploded diagram, the further components of the locking means 140 include a lock 142, a lock door 144, and a lock cover 146. In the preferred embodiment, the locking means 140 is an Abloy Lock Delmar CL200E manufactured by Abloy Security, Inc. located in Irving, Tex. Alternatively, any other locking means 140 known to one skilled in the art may be used provided that it is used to lockingly secure the drug testing home device 100.

Additionally, a fan unit 148 is provided as a cooling means or preventive heating mechanism for the drug testing home device 100. In the preferred embodiment, any fan unit 148 known to one skilled in the art may be used provided that it is used to cool or prevent the overheating of the drug testing home device 100.

In the preferred embodiment, the various other components illustrated in the exploded diagram are used in the integration of all of the components described above in the complete assembly of the drug testing home device 100.

Alternatively, in lieu of a drug testing home device 100, a drug testing kiosk device 102, as illustrated in FIGS. 2 and 3, may be used as the computer hardware to accomplish the purposes of Applicant's invention described herein. Referring to FIGS. 2 and 3, the drug testing kiosk device 102 is illustrated. The drug testing kiosk device 102 is designed to be placed or installed in convenient public facilities such as the lobby of buildings or other convenient locations for access and use by the participants to comply with the participant's testing schedule, described in further detail below.

The drug testing kiosk device 102 comprises a kiosk housing 156 that provides the exact same components as the drug testing home device 100 including but not limited to the finger print reader 114 and the camera 122. The drug testing kiosk device 102 also further provides the liquid crystal display screen 110, the central processing unit computer 124, and the fan unit 148 components that, although are not the exact same devices as those used in the drug testing home device 100, likewise operate and perform the same functions in each. A printer 160 and a printer receipt report outlet 162 are used to generate and display the testing results to the participant.

Additionally, the drug testing kiosk device 102 also provides the breathalyzer or multi-testing device 118, except that in this device, the breathalyzer or multi-testing device 118 is contained within a breathalyzer holder 158 lockingly secured to the kiosk housing 156 to prevent the unauthorized tampering of the breathalyzer or multi-testing device 118 by the participant. The breathalyzer or multi-testing device 118 is also provided with a microphone 164 and a breathalyzer hole 166, the operation and use of which are each described in further detail below.

The computer system consists of the computer hardware (i.e., the drug testing home device 100 as illustrated in FIG. 1 or the drug testing kiosk device 102 as illustrated in FIGS. 2 and 3) and the computer software. Preferably, to install and run the computer software on this computer system, the computer system should provide at least Microsoft Windows 2000 or newer with the most recently available service pack installed, Microsoft SQL and web server software, and Microsoft Internet Explorer 4.0 or newer, preferably 6.0. Additionally, if the computer system 24 is running a firewall, the firewall must be configured to allow the computer software to make TCP (outbound) calls. Alternatively, as computers and their components and the communication between them are well known in the art, it is also contemplated that any computer hardware, compatible type, version, or size made by any manufacturer is acceptable as the computer hardware to accomplish the intended purposes of Applicant's invention.

Figure 4:
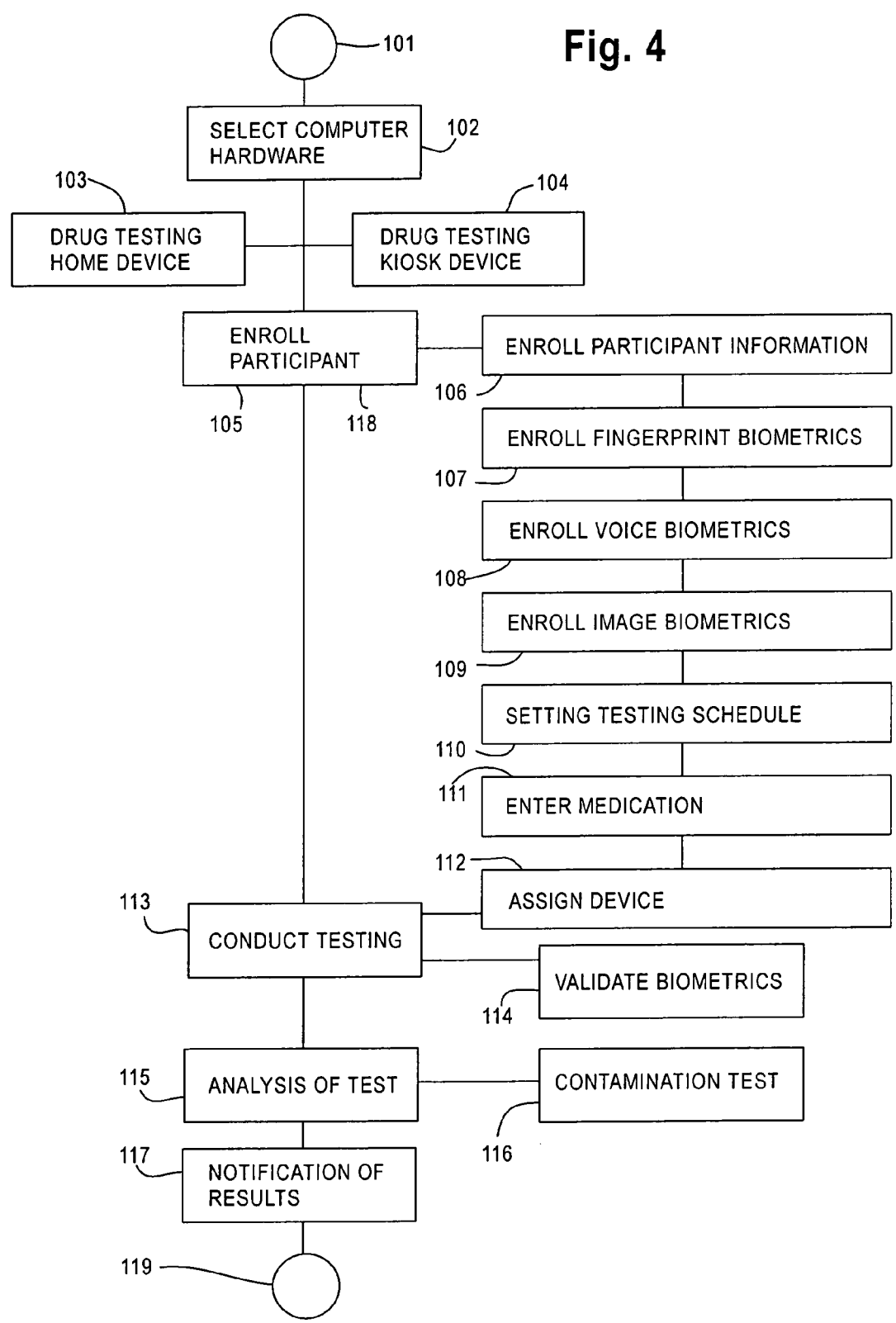
FIG. 4 is a flowchart illustrating the basic operation of Applicant's computer system for determining alcohol and drug testing.

Referring to FIG. 4, there is illustrated a schematic diagram of the basic operation of Applicant's unique apparatus and method for passive testing of alcohol and drug abuse for determining alcohol and/or drug testing.

In Step 101, the process begins. If the participant (also referred to as subject) desires to begin, proceed to Step 102. If the participant desires not to begin, proceed to Step 119. In Step 102, the participant selects which of the computer hardware to use. If the participant has been provided with the drug testing home device 100, proceed to Step 103. If the participant has not been provided with the drug testing home device 100 and/or has elected the drug testing kiosk device 102, proceed to Step 104.

In Step 103, if the drug testing home device 100 is the computer hardware used by the participant, proceed to Step 105. If not, proceed back to Step 102.

In Step 104, if the drug testing kiosk device 102 is the computer hardware used by the participant, proceed to Step 118. If not, proceed back to Step 102.

Figure 5:
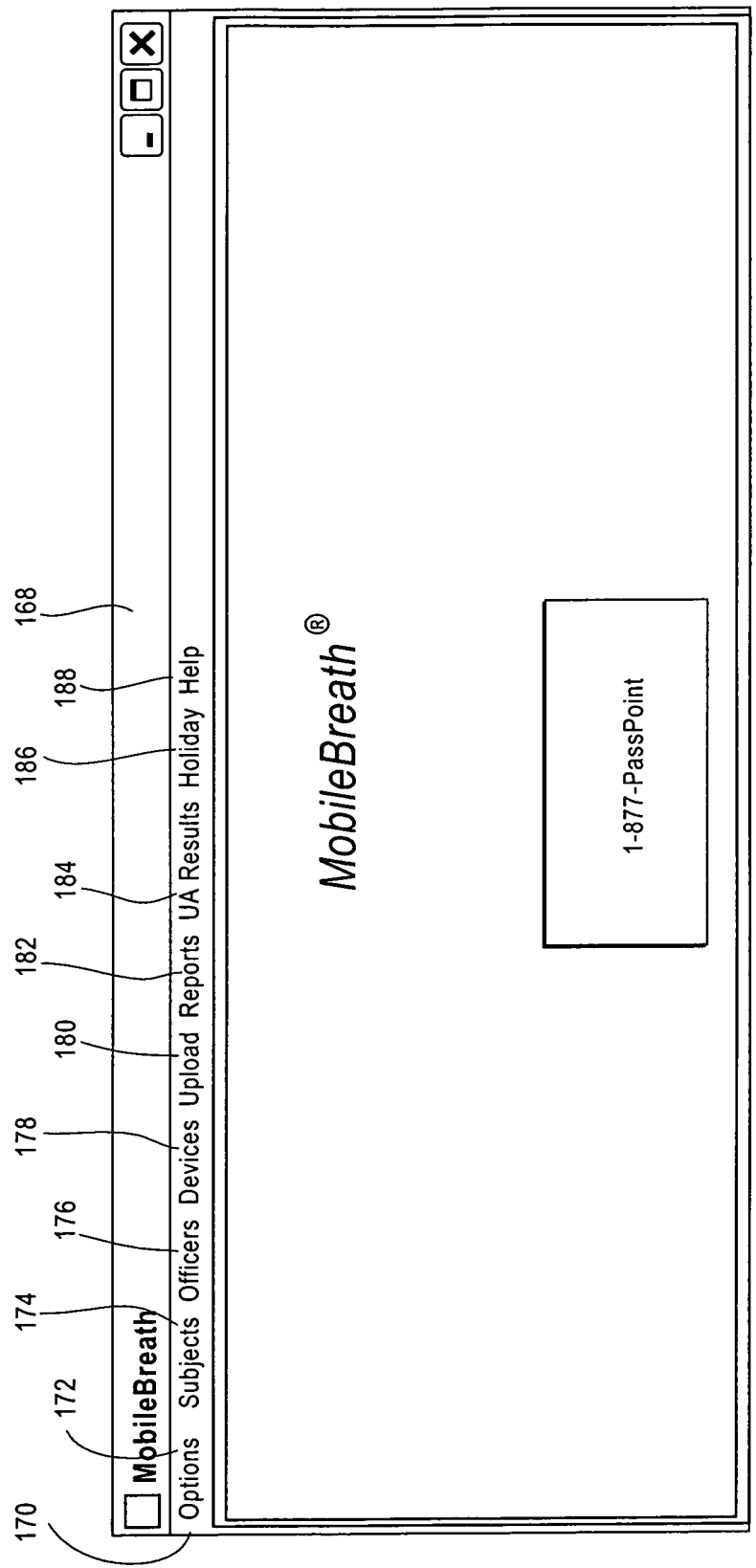
FIG. 5 is a diagram of the home interface screen of the computer software for the drug testing home device.

In Step 105, if the participant is already entered into the computer system, proceed to Step 113. If the participant is not entered or enrolled into the computer system, proceed to enroll the participant into the system using the enrollment process. The drug testing home device 100 provides a home interface screen 168, as illustrated in FIG. 5, on the lcd display screen 110. The home interface screen 168 comprises a menu bar 170 which provides access to all of the options of the home interface screen 168.

The menu bar 170 provides an options heading 172, a subjects heading 174, an officers heading 176, a devices heading 178, an upload heading 180, a reports heading 182, a UA results heading 184, a holidays heading 186, and a help heading 188.

Figure 6:
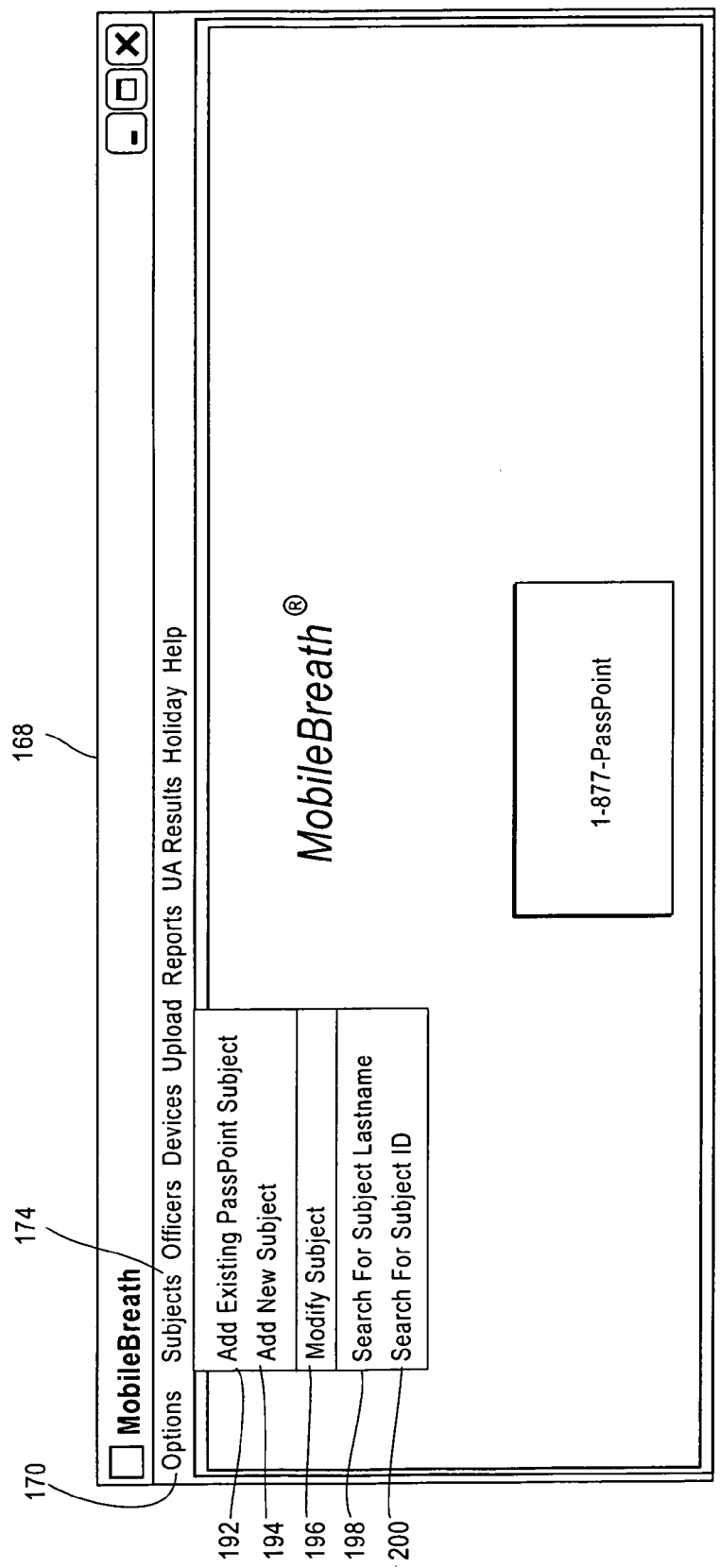
FIG. 6 is a diagram of the drop down menu resulting from the selection of the subjects heading from the menu bar of the home interface screen.
Figure 7:
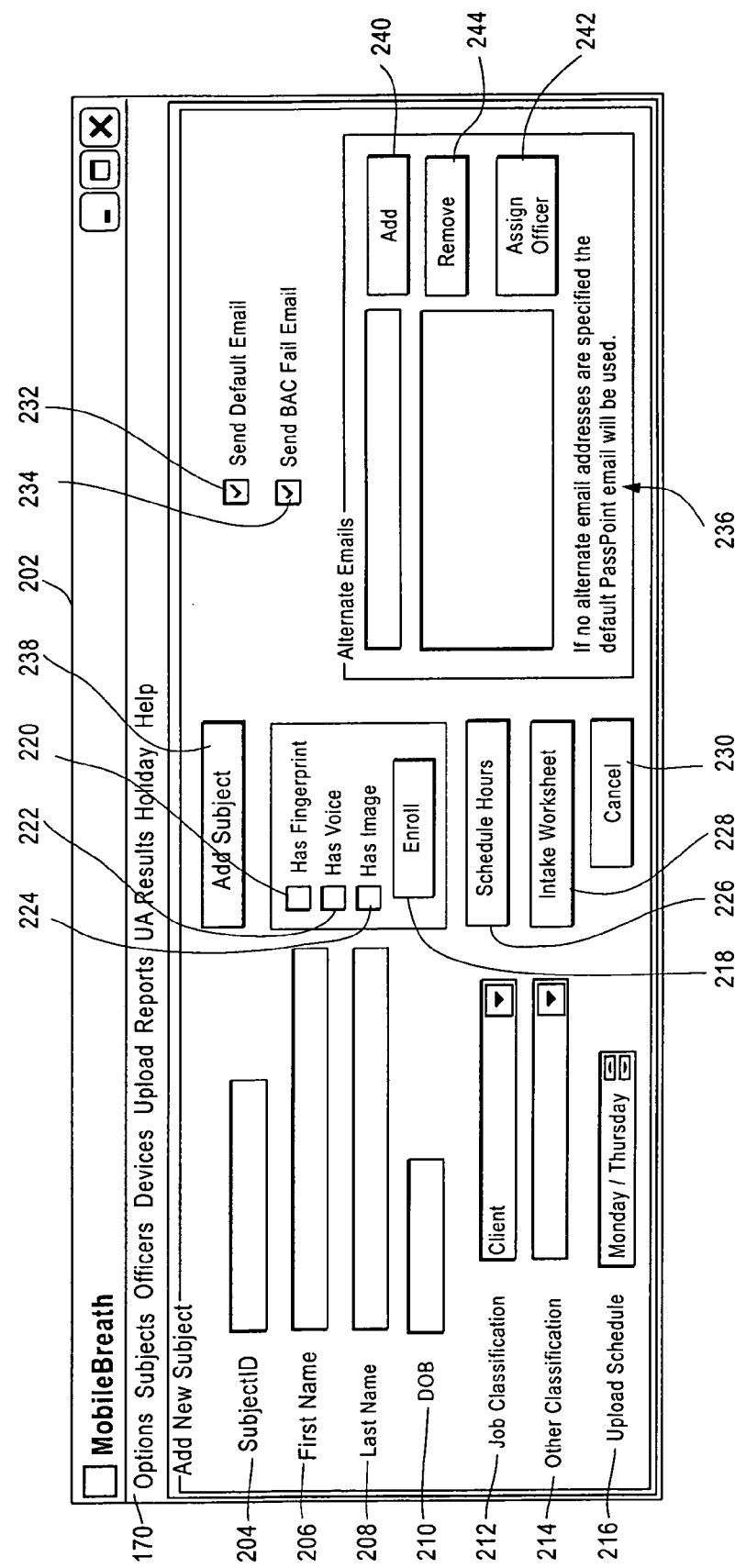
FIG. 7 is a diagram of the add new subject pane resulting from the selection of the add new subject option from the drop down menu of the subjects heading from the menu bar of the home interface screen.

Using the menu bar 170, the subjects heading 174 is selected, using the touch pad 112 of the drug testing home device 100, which displays a subjects heading drop down menu 190, as illustrated in FIG. 6. The subjects heading drop down menu 190 provides an add existing passpoint subject option 192, add new subject option 194, modify subject option 196, search for subject lastname option 198, and search for subject id option 200. Selecting the add new subject option 194 displays the add new subject pane 202, as illustrated in FIG. 7. This process may be designated by the nomenclature of "Subjects>Add New Subject". The "Subject" refers to the subjects heading 174 and the "Add New Subject" refers to the add new subject option 194. Alternatively, it is contemplated that this process of accessing the add new subject pane 202 may be loaded using a toolbar icon (not illustrated) which provides an icon to select to accomplish this same step.

In FIG. 7, the add new subject pane 202 provides the information to enroll the participant into the system. In the preferred embodiment, the add new subject pane 202 provides a subject id box 204, a first name box 206, a last name box 208, a dob box 210, a job classification box 212, an other classification box 214, an upload schedule box 216, an enroll button 218, a has fingerprint box 220, a has voice box 222, a has image box 224, a schedule hours button 226, an intake worksheet button 228, a cancel button 230, a send default email box 232, a send bac fail email 234, an alternate emails section 236, and an add subject button 238.

The participant enters or completes the add new subject pane 202 in four steps. In Step 106, the participant enters the appropriate information into the subject id box 204 (i.e., this is a number assigned to the participant by their supervisor, the participant's case number, the participant's case docket number, or any other desired number provided that it is unique to the participant), the first name box 206 (i.e., the first name of the participant), the last name box 208 (i.e., the last name of the participant), the dob box 210 (i.e., the date of birth of the participant), the job classification box 212 (i.e, this is the case program classification for the participant which includes but is not limited to client, drug court, adult supervision, or any other type of classification desired), the other classification box 214 (i.e., if the proper classification is not available or provided in the job classification box 212, a different type of classification can be entered here), the upload schedule box 216 (i.e., this represents the extent of the testing days for the participant). The participant also completes the alternate emails section 236 by clicking on the assign officer button 242 for a pre-defined list of officers to select from to enter the e-mail of the particular officer(s) responsible for or are authorized to receive notifications regarding the participant. Alternatively, if the officer is not provided in the pre-defined list of officers, the participant may click on the add button 240 to manually enter the email of the officer or another person (such as a supervising officer, regular officer, treatment person, judge, or any other person interested in and authorized to receive the testing information of the participant). If any e-mail has been entered incorrectly or is desired to be removed, clicking on the remove button 244 allows the participant to remove any such incorrect e-mail. The participant may also check the send default email box 232 and/or the send bac fail email 234 such that the persons whose e-mails are entered will receive all e-mails and/or just the e-mails where the participant's blood alcohol failed the test. Once completed, proceed to Step 107.

Figure 8:
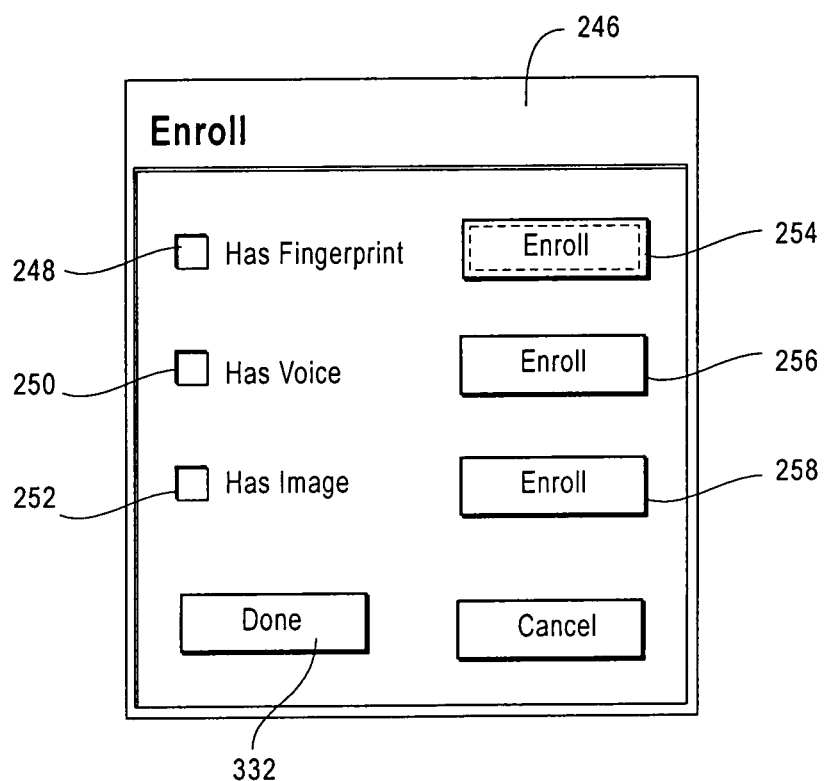
FIG. 8 is a diagram of the enroll pane resulting from the selection of the enroll button from the add new subject pane.

In Step 107, the participant's biometric information is enrolled into the system. Initially, the has fingerprint box 220, has voice box 222, and has image box 224 are shown as blank. This means that the participant's biometric fingerprint, voice, and image has not yet been entered into the system. Clicking on the enroll button 218 displays an enroll pane 246, as illustrated in FIG. 8. The enroll pane 246 provides a has fingerprint selection box 248, a has voice selection box 250, and a has image selection box 252. Each of these boxes are likewise shown as blank as none of this biometric information has been entered into the system for the participant. The participant chooses one to enroll by clicking one of the corresponding enroll buttons 254 (i.e., finger enroll button), 256 (i.e., voice enroll button), and/or 258 (i.e., image enroll button).

Figure 9:
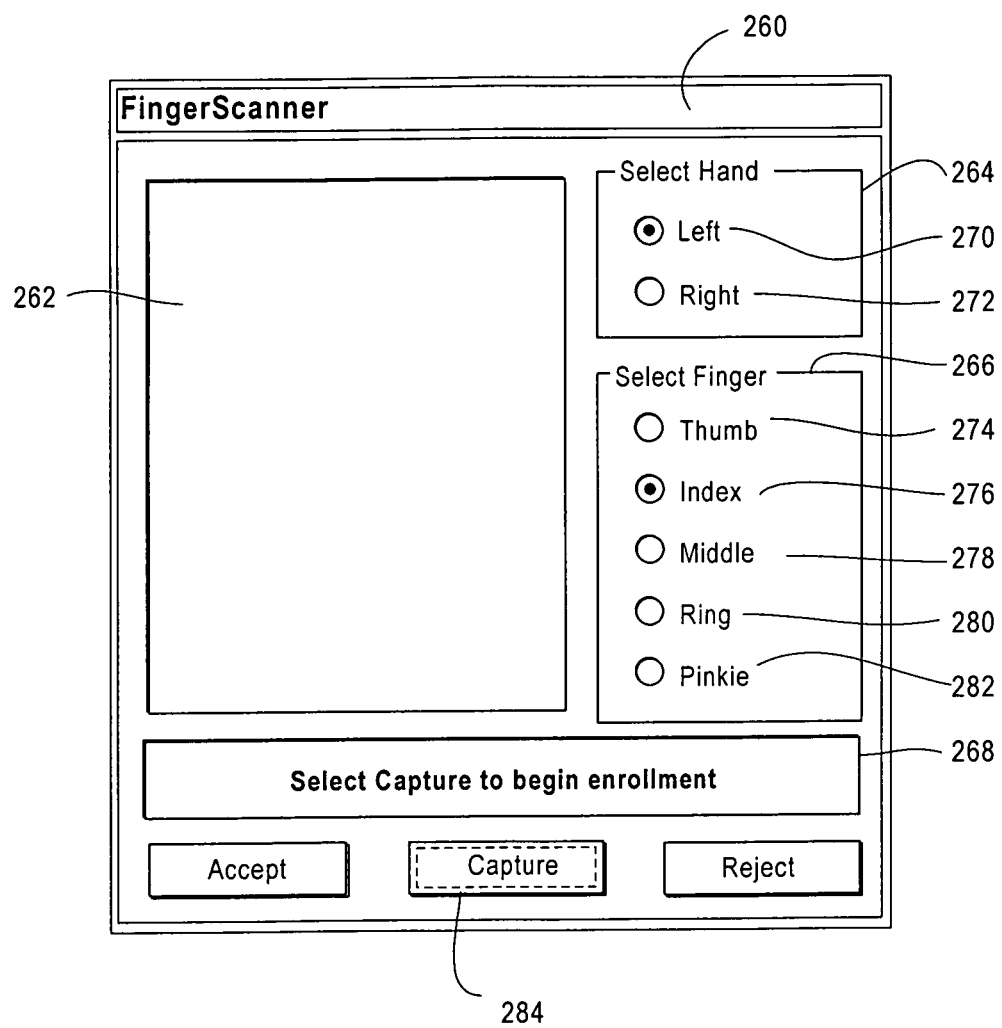
FIG. 9 is a diagram of the finger scanner pane resulting from the selection of the finger enroll button from the enroll pane to begin the enrollment process of the finger print biometric of the participant.
Figure 10:
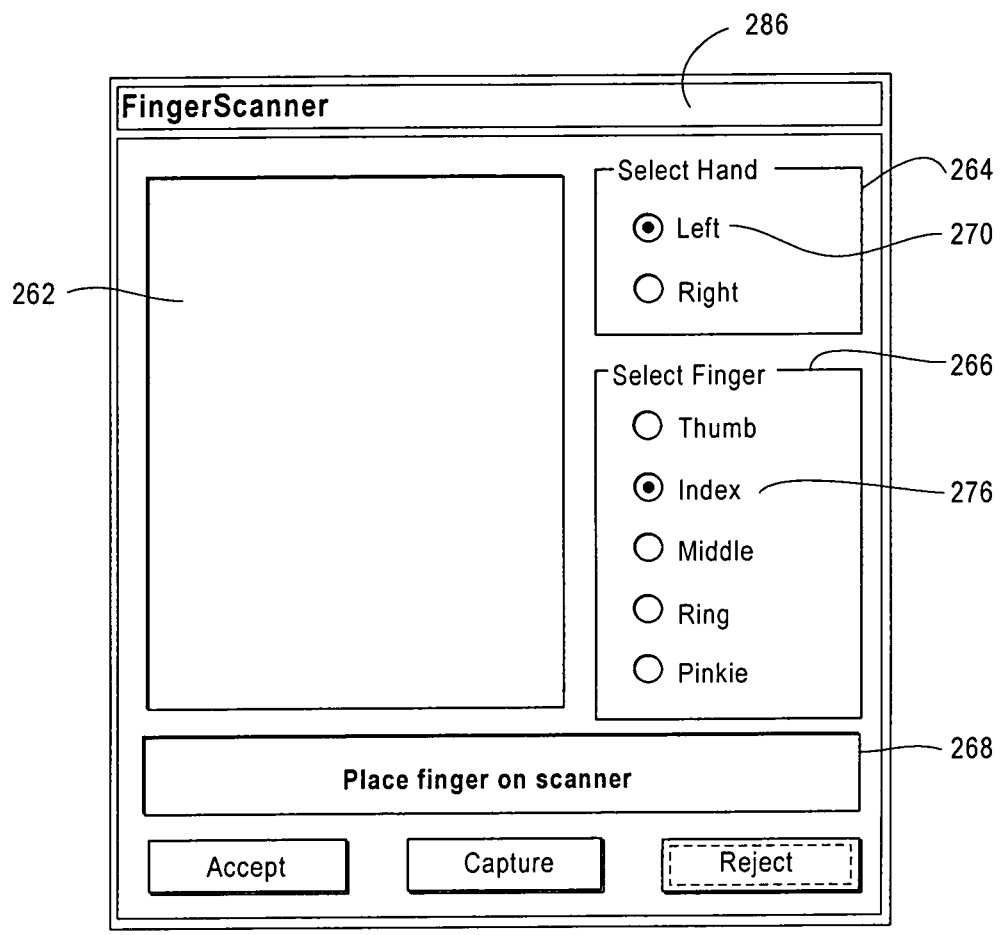
FIG. 10 is a diagram of the finger scanner pane resulting from the selection of the capture button during the enrollment process of the finger print biometric of the participant.

To proceed with enrolling the participant's fingerprint biometric information (also referred to as "finger print enrollment process"), clicking on the enroll button 254 displays a fingerscanner pane 260, as illustrated in FIG. 9. The fingerscanner pane 260 provides a finger image window 262, a select hand section 264, a select finger section 266, and a message box 268. The participant selects which hand to use by clicking, in the select hand section 264, the left selection 270 (i.e., for the left hand) or by clicking the right selection 272 (i.e., for the right hand). In the non-limiting example provided, the left selection 270 is selected identifying the left hand. The participant then selects which finger on the selected hand to use by clicking, in the select finger section 266, the thumb selection 274 (i.e., for the thumb finger), the index selection 276 (i.e., for the index finger), the middle selection 278 (i.e., for the middle finger), the ring selection 280 (i.e., for the ring finger), and the pinkie selection 282 (i.e., for the pinkie finger). In the non-limiting example provided, the index selection 276 is selected identifying the index finger for the left hand. Once the hand and finger are selected, the message box 268 displays the message "Select Capture to begin enrollment." Clicking on the capture button 284 begins the enrollment for the selected hand and finger and displays a fingerscanner pane 286, as illustrated in FIG. 10.

Figure 11:
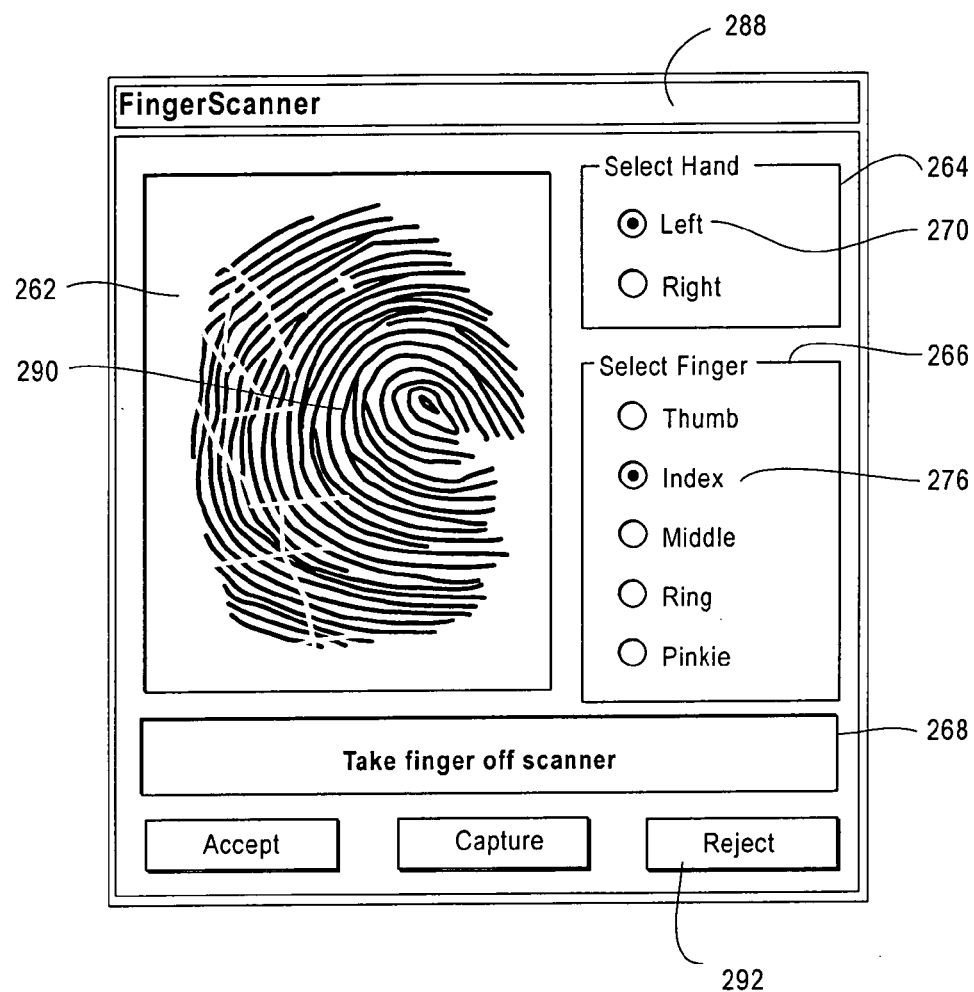
FIG. 11 is a diagram of the finger scanner pane resulting from the finger print reader reading the selected finger of the selected hand of the participant during the enrollment process of the finger print biometric of the participant.

The fingerscanner pane 286 is the same pane as the fingerscanner pane 260, except that the participant's selection of the selected hand in the left selection 270 of the select hand section 264 and the selected finger in the index selection 276 of the select finger section 266 are shown; and the message box displays the message "Place finger on scanner." Upon placing the selected finger of the selected hand in the finger print reader 114 of the drug testing home device 100, a fingerscanner pane 288 is displayed, as illustrated in FIG. 11.

Figure 12:
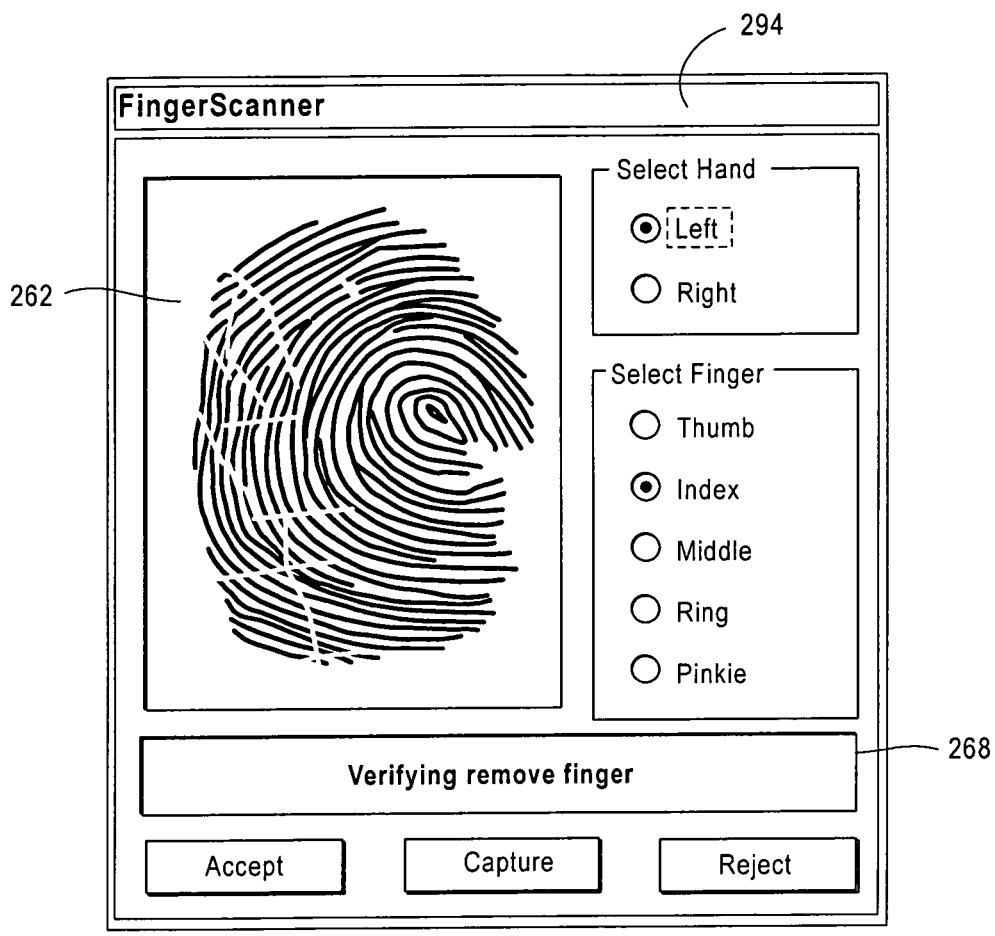
FIG. 12 is a diagram of the finger scanner pane resulting from the removal and verification of the selected finger of the selected hand of the participant from the finger print reader during the enrollment process of the finger print biometric of the participant.
Figure 13:
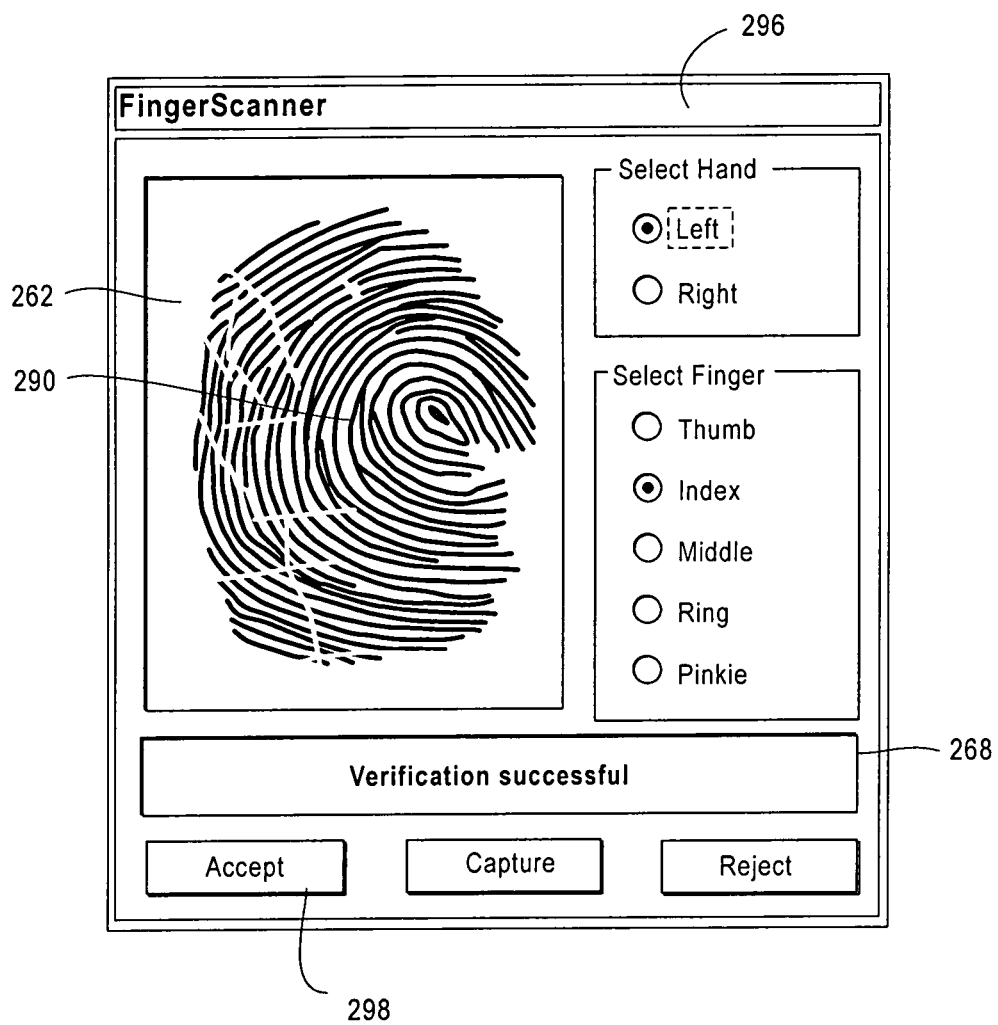
FIG. 13 is a diagram of the finger scanner pane resulting from the successful verification of the selected finger of the selected hand of the participant to complete the enrollment process of the finger print biometric of the participant.

The fingerscanner pane 288 displays in the finger image window 262 the actual image 290 of the selected hand and finger which, in this non-limiting example, is the index finger of the left hand. The selected hand in the left selection 270 of the select hand section 264 and the selected finger in the index selection 276 of the select finger section 266 likewise confirm the selected hand and finger. If the actual image 290 appears to be blurry, not complete, or otherwise not correct in any manner, clicking on the reject button 292 will allow the process to be repeated. If the actual image 290 appears correct, the message box displays the message "Take finger off scanner." Upon removing the selected finger from the finger image window 262, a fingerscanner pane 294 is displayed, as illustrated in FIG. 12. The message box displays the message "Verifying remove finger" to confirm that the participant has, in fact, removed the selected hand and finger from the finger image window 262. When verified, the fingerscanner pane 296 is displayed, as illustrated in FIG. 13. The message box displays the message "Verification successful" confirming that the actual image 290 displayed in the finger image window 262 is a successful scan of the actual image 290 of the selected hand and finger and of acceptable quality to use. Clicking on the accept button 298 accepts the scan of the actual image 290 and enters this finger print biometric information into the system and returns the participant to the enroll pane 246, as illustrated in FIG. 8. The process could be continually repeated in the same manner to enroll each of the hand and fingers of the participant. Once the finger prints of the participant have been enrolled into the system, clicking the done button 332 will return the participant to the add new subject pane 202, as illustrated in FIG. 7. Although not shown, the has fingerprint box 220 will then be changed from a blank to a check mark to confirm that the finger print biometric information of the participant has now been enrolled into the system. Once completed, proceed to Step 108.

Figure 14:
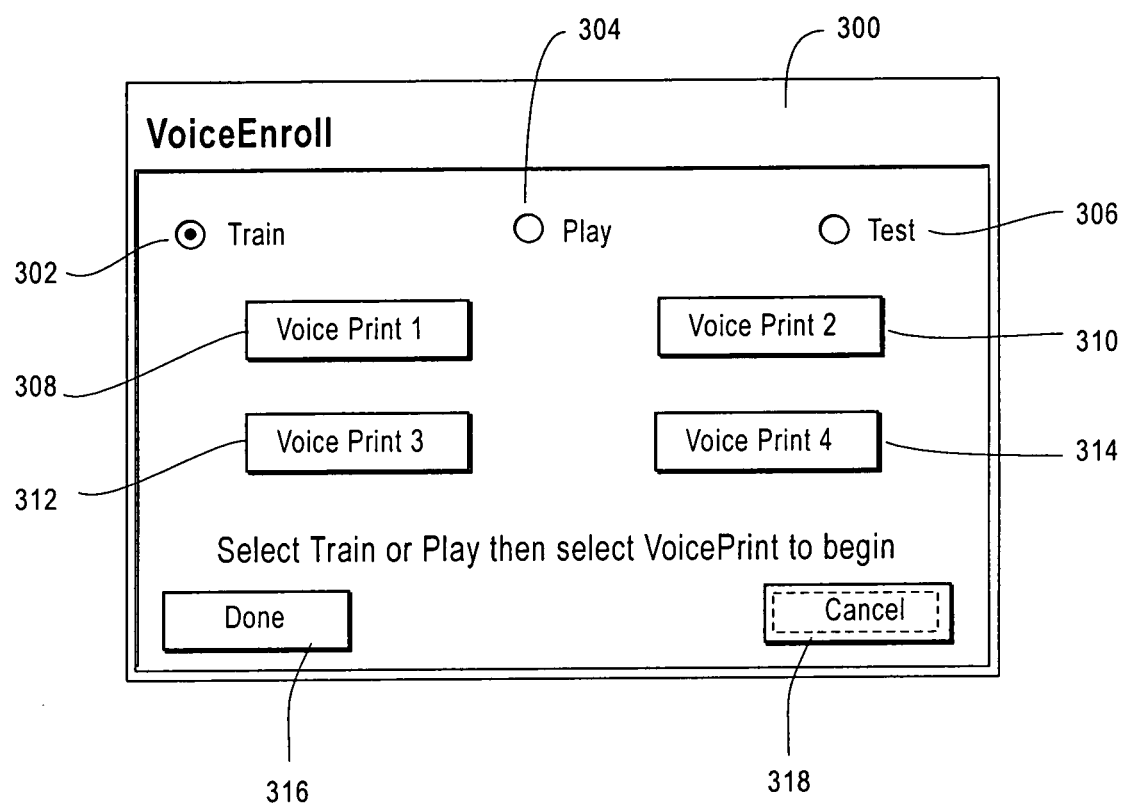
FIG. 14 is a diagram of the voice enroll pane resulting from the selection of the voice enroll button from the enroll pane to begin the enrollment process of the voice biometric of the participant.

In Step 108, the participant continues to proceed with enrolling the participant's voice biometric information (also referred to as "voice enrollment process") by clicking on the enroll button 218 again re-displays the enroll pane 246, as illustrated in FIG. 8. Although not shown, the has fingerprint box 248 will then be changed from a blank to a check mark to confirm that the finger print biometric information of the participant has now been enrolled into the system. The has voice selection box 250 and the has image selection box 252 will each remain blank as this biometric information has not yet been entered into the system. The participant chooses the next one to enroll by clicking one of the corresponding enroll buttons 256 and/or 258. To proceed with enrolling the participant's voice biometric information, clicking on the enroll button 256 displays a voice enroll pane 300, as illustrated in FIG. 14.

The voice enroll pane 300 provides a train selection 302 (i.e., allows the participant to proceed to enroll the voice of the participant into the system), a play selection 304 (i.e., allows the participant to play back a voice phrase that has previously been stored), a test selection 306 (i.e., allows a supervisor or other authorized person to test a particular phrase of the participant to confirm its accuracy), and voice print buttons 308, 310, 312, and 314. If the train selection 302 is selected and clicking on the voice print button 308, the system will audibly state a phrase. In the preferred embodiment, the phrase is randomly selected from a stock of suggested phrases that are preferably at least three (3) seconds long. Non-limiting examples of such phrases include but are not limited to "Have no friends not equal to yourself;" "Learning without thought is labor lost;" "Thought without learning is perilous;" "Diligence is the mother of good fortune;" etc. . . . , or any other unlimited examples of desired phrases. The participant speaks the suggested phrase. A voice recording of the participant speaking the phrase is then stored into the system. Alternatively, to confirm a more uniform and consistency and the possibility of a better recording, the participant may be required to repeat the suggested phrase, for example, three (3) times with the best recording of the suggested phrase being stored into the system. When completed, the participant repeats the steps with the voice print buttons 310, 312, and 314, each time recording a different suggested phrase to record for the participant. In this manner, there are multiple voice recordings of the participant enrolled into the system which may be used later in voice validation and testing, described in further detail below. If for any reason, this voice enrollment process is not working properly or the participant must cancel from the voice enrollment, clicking on the cancel button 318 returns the participant to the add new subject pane 202, as illustrated in FIG. 7. When all the voice recordings are recorded and completed, clicking on the done button 316 returns the participant to the enroll pane 246, as illustrated in FIG. 8. If the voice of the participant has been enrolled into the system, clicking the done button 332 will return the participant to the add new subject pane 202, as illustrated in FIG. 7. Although not shown, the has voice box 222 will now be changed from a blank to a check mark to confirm that the voice biometric information of the participant has also been enrolled into the system. Once completed, proceed to Step 109.

Figure 15:
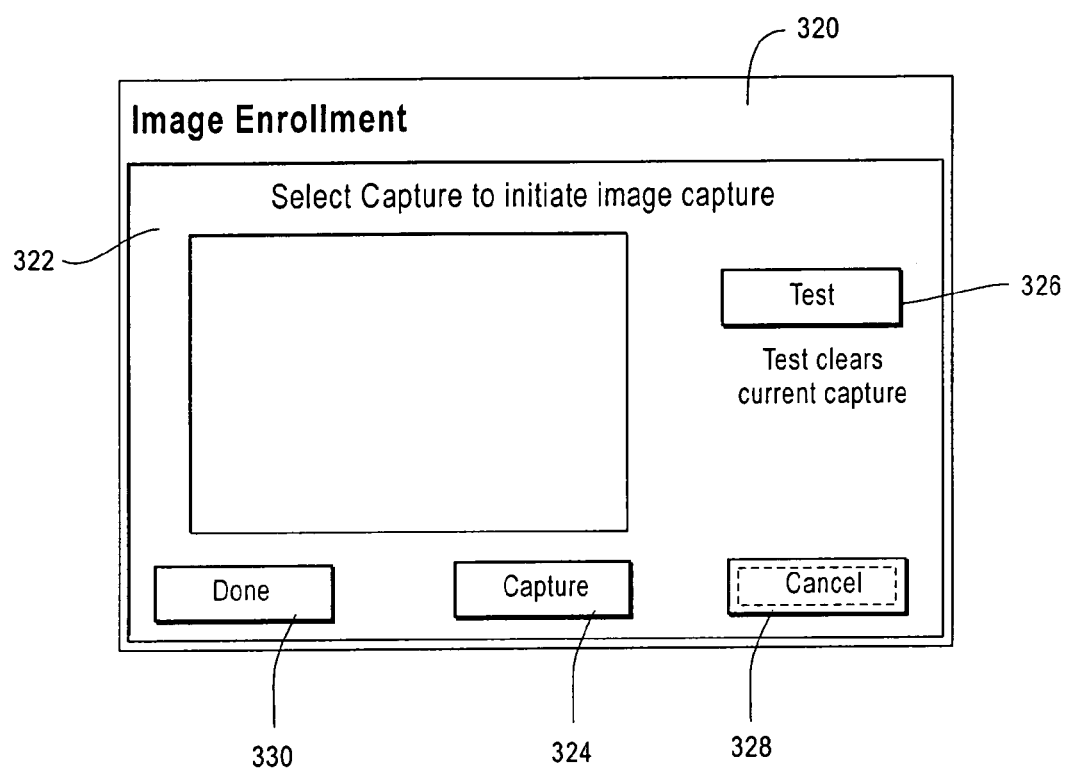
FIG. 15 is a diagram of the image enrollment pane resulting from the selection of the image enroll button from the enroll pane to begin the enrollment process of the image biometric of the participant.

In Step 109, the participant continues to proceed with enrolling the participant's image biometric information (also referred to as "image enrollment process" or "face recognition process") by clicking on the enroll button 218 again re-displays the enroll pane 246, as illustrated in FIG. 8. Although not shown, the has voice box 250 will now be changed from a blank to a check mark to confirm that the voice biometric information of the participant has also been enrolled into the system. The has image selection box 252 will remain blank as this biometric information has not yet been entered into the system. To proceed with enrolling the participant's image biometric information, clicking on the enroll button 258 displays an image enroll pane 320, as illustrated in FIG. 15.

The image enroll pane 320 provides an image window 322 and a capture button 324. Clicking on the capture button 324, the camera 122 of the drug testing home device 100, records the image of the participant. In the preferred embodiment, the facial image of the participant is recorded three (3) times with each facial image compared for consistency. If the images are found consistent and acceptable, the facial image of the participant is enrolled into the system and the actual facial image is displayed into the image window 322 (not shown). If the participant is not satisfied with the image recorded, clicking on the test button 326 clears the recorded images. The participant can then repeat the image enrollment process. Likewise, if for any reason this image enrollment process is not working properly or the participant must cancel from the image enrollment, clicking on the cancel button 328 returns the participant to the add new subject pane 202, as illustrated in FIG. 7. When the images of the participant are recorded and completed, clicking on the done button 330 returns the participant to the enroll pane 246, as illustrated in FIG. 8. If the image of the participant has been enrolled into the system, clicking the done button 332 will return the participant to the add new subject pane 202, as illustrated in FIG. 7. Although not shown, the has image box 224 will now be changed from a blank to a check mark to confirm that the image biometric information of the participant has also been enrolled into the system. Once completed, proceed to Step 110.

Alternatively, prior to beginning Step 110, the participant continues to proceed with enrolling the participant's volatile organic compound (i.e., voc) gas and the pH level biometric information (also referred to as "voc and/or pH enrollment process"). Using the similar process as described above for the enrollment of the participant's other biometrics, the participant blows into the multi-testing device 118 as described above and illustrated in FIGS. 43(A)-(F) (i.e., should this device be used instead of the breathalyzer device 118), the participant blows into the multi-testing device 118. The multi-testing device 118 then records a volatile organic compound (i.e., voc) gas reading and the pH level reading of the participant. In the preferred embodiment, the volatile organic compound (i.e., voc) gas reading and/or the pH level reading of the participant are recorded for, in a non-limiting example, three (3) times with each reading compared for consistency. If the readings of each of the volatile organic compound (i.e., voc) gas reading and/or the pH level reading are found consistent and acceptable, the volatile organic compound (i.e., voc) gas reading and/or the pH level biometrics of the participant are also enrolled into the system for the participant.

Figure 16:
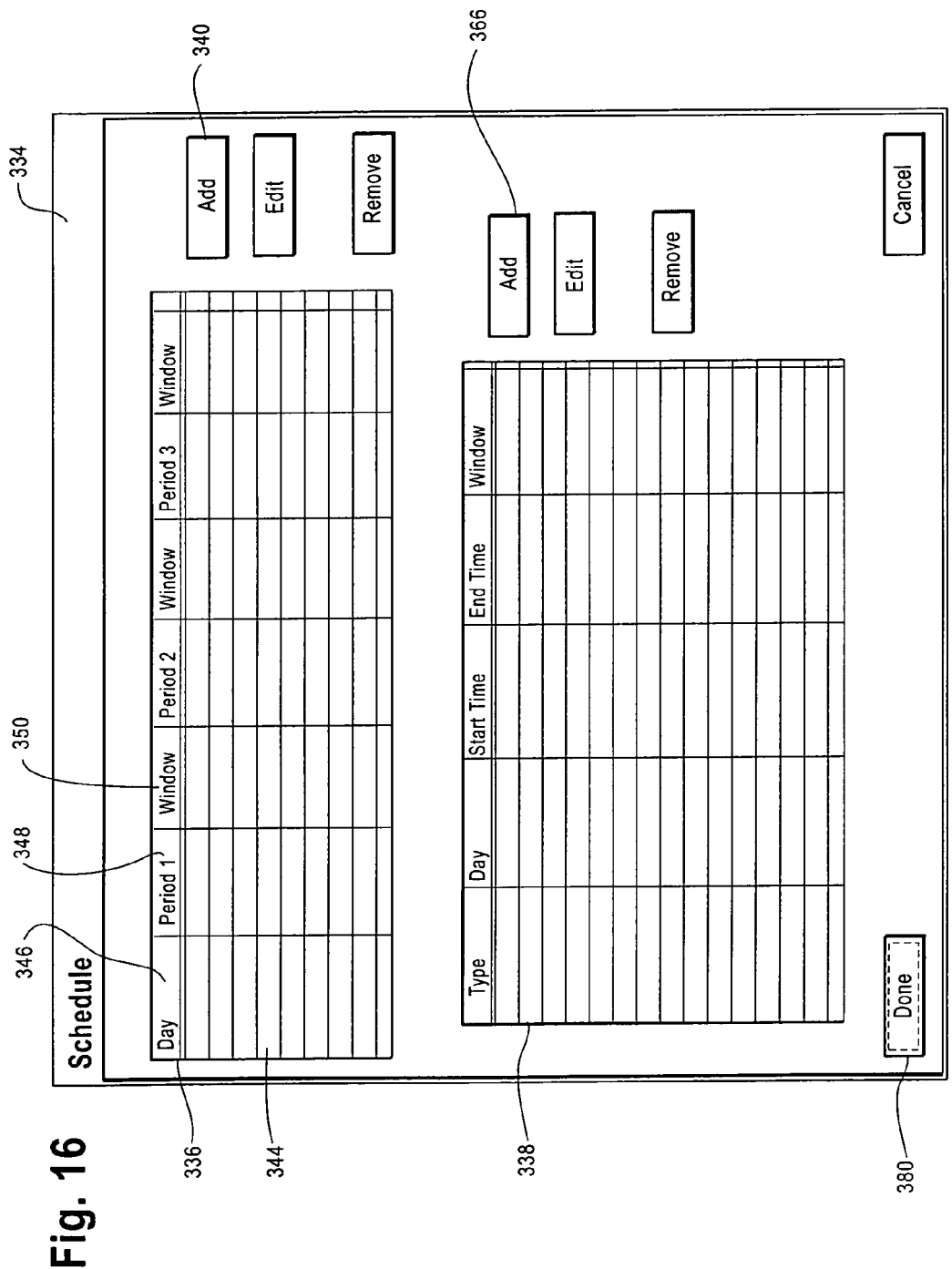
FIG. 16 is a diagram of the schedule pane resulting from the selection of the schedule hours button from the add new subject pane to begin setting the testing schedule of the participant.

In Step 110, the testing schedule of the participant is scheduled (also referred to as "testing schedule enrollment process"). Clicking on the schedule hours button 226 displays a schedule pane 334, as illustrated in FIG. 16. The schedule pane 334 provides a set schedule section 336 and a random schedule section 338. The set schedule section 336 is used to set the participant's fixed testing schedule. The random schedule section 338 is used to set the participant's random testing schedule. Alternatively, the random schedule section 338 may also be used to set the participant's fixed testing schedule in lieu of setting it in the set schedule section 336, if desired.

The set schedule section 336 provides a chart 344 which defines a day column 346, a period column 348, and a window column 350. Each of these columns are repeated several times. The day column 346 represents the particular day of the week (i.e., Monday through Sunday), the period column 348 represents the particular time of the day (i.e., any time during a 24 hour period), and the window column 350 represents a tolerance or grace testing period before or after the particular time of the day that is permitted to perform the test if the participant is early or late to their testing time (i.e, a non-limiting example is 15 minutes, which means the window to take a test can occur from as early as 15 minutes prior to the particular time of day shown in the period column 348 and up to 15 minutes after the particular time of day shown in the period column 348). Initially, the set schedule section 336 is shown as blank. This means that the participant's testing schedule has not yet been entered into the system.

Figure 17:
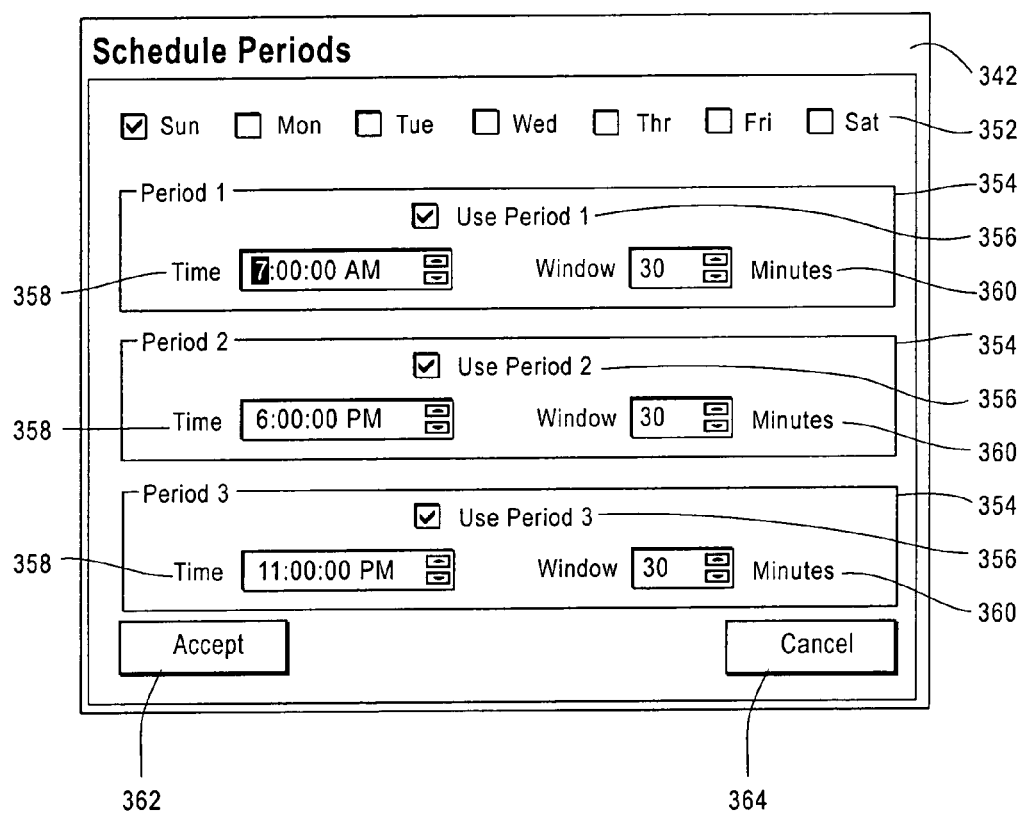
FIG. 17 is a diagram of the schedule periods pane resulting from the selection of the fixed schedule add button from the schedule pane during setting the testing schedule of the participant.

If the participant's fixed testing schedule is to be set, in the set schedule section 336, clicking on the add button 340 displays a schedule periods pane 342, as illustrated in FIG. 17. The schedule periods pane 342 provides the day selections menu 352 consisting of Sunday through Saturday and several period selections menu 354. In the preferred embodiment, the participant selects the first day that testing will begin and appropriately selects that selected day from the day selections menu 352. In the non-limiting example, the day of Sunday is selected. For that selected day, the participant then selects a fixed testing time from one or all of the period selections menu 354. For example, if the participant is to be tested for all of the testing times from the period selections menu 354, the use period box 356 are each selected with a check mark (as illustrated). In each of the period selections menu 354, the time 358 and the window 360 are each then set. In the non-limiting example, the first fixed test is scheduled for Sunday at 7:00 am with a grace testing period of thirty (30) minutes; the second fixed test scheduled for Sunday is at 6:00 pm with a grace testing period of thirty (30) minutes; and the third fixed test scheduled for Sunday is at 11:00 pm with a grace testing period of thirty (30) minutes. If for any reason, this schedule process is not working properly or the participant must cancel from the schedule, clicking on the cancel button 364 returns the participant to the schedule pane 334, as illustrated in FIG. 16. When the fixed testing schedule is completed or set, clicking on the accept button 362 returns the participant to the schedule pane 334, as illustrated in FIG. 16. The process is continually repeated in the same manner to set the testing schedule for any or all of the remaining days of the week. Once the fixed testing schedule has been completed or set, the random testing schedule can be set which likewise is initially shown as blank as the participant's random testing schedule has not yet been entered into the system.

Figure 18:
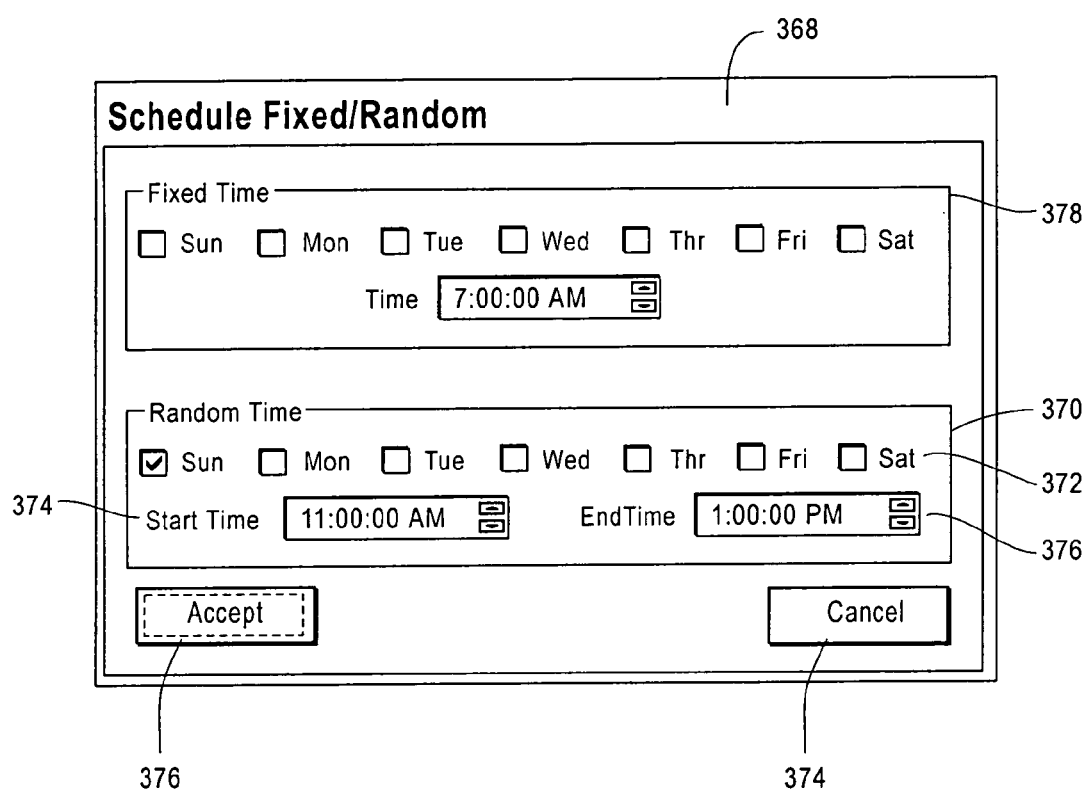
FIG. 18 is a diagram of the schedule random periods pane resulting from the selection of the random schedule add button from the schedule pane during setting the testing schedule of the participant.
Figure 20:
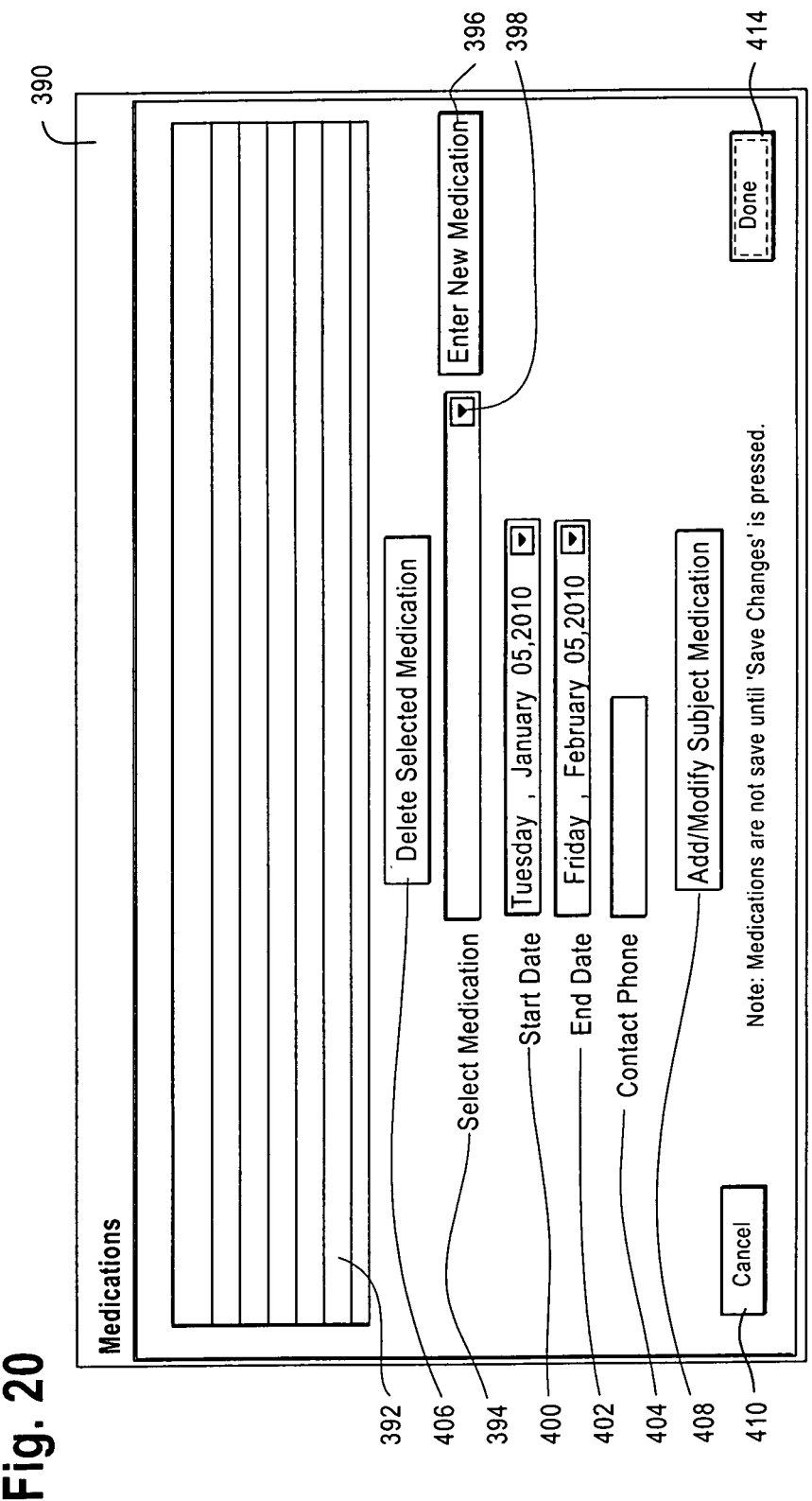
FIG. 20 is a diagram of the medications pane resulting from the selection of the medications button from the intake worksheet pane during the entering the history and medications of the participant.

To complete or set the random testing schedule, clicking the add button 366 in the random schedule section 338 of FIG. 16 displays a schedule random periods pane 368, as illustrated in FIG. 18. The schedule random periods pane 368 provides the random time section 370 providing a random day selections menu 372 consisting of Sunday through Saturday and a random start time 374 and a random end time 376. In the preferred embodiment, the participant selects the first random day that testing will begin and appropriately selects that selected day from the random day selections menu 372. In the non-limiting example, the day of Sunday is selected. For that selected day, the participant then selects a random testing time that begins with the start time 374 and ends with the end time 376. In the preferred embodiment, if the participant is to be randomly tested on Sunday which is also a fixed testing day (as described in the example above), the random testing times must be at a different time than the fixed testing times already scheduled for the participant. In the non-limiting example, the random start time is scheduled for Sunday at 11:00 am with an end time of 1:00 pm. If for any reason, this random schedule process is not working properly or the participant must cancel from the schedule, clicking on the cancel button 374 returns the participant to the schedule pane 334, as illustrated in FIG. 16. When the random testing schedule is completed or set, clicking on the accept button 376 returns the participant to the schedule pane 334, as illustrated in FIG. 16. The process is continually repeated in the same manner to set the random testing schedule for any or all of the remaining days of the week. Additionally, as previously mentioned, the participant's fixed testing schedule may be completed or set using the fixed time 378 in the schedule random periods pane 368, as illustrated in FIG. 18. Once the fixed testing schedule and random testing schedule has been entered and is set for the participant, clicking the done button 380 (see FIG. 16) will return the participant to the add new subject pane 202, as illustrated in FIG. 7. Once completed, proceed to Step 111.

In Step 111, the medications and intake information of the participant are completed (also referred to as the "medications and/or intake enrollment process"). Clicking on the intake worksheet button 228 displays an intake worksheet pane 382, as illustrated in FIG. 19. The intake worksheet pane 382 provides a list of questions 384 accompanied by answer selections 386 to each of the questions 384. The purpose of the questions is to assist in understanding the participant's lifestyle to determine what, if any, impact this may have on the testing process for the participant. Additionally, clicking on the medications button 388 displays a medications pane 390. The medications pane 390 provides a medications window 392 which initially is shown as blank until the participant's medications are entered into the system. A select medications entry 394 is used to enter a medication that the participant is taking using a drop down menu 398 of possible medications to select from. Clicking on the enter new medication button 396 also provides a means to manually enter the participant's medication into the select medications entry 394. The time period that the selected medication to be taken is entered at the start date 400 and the end date 402 and, just in case the needs arises, a phone number of a person to contact on the participant's behalf is entered at contact phone 404. Should the participant desire to delete an entered medication, selecting the entered medication from the medication window 392 and clicking on the delete selected medication button 406 will delete the medication. Should the participant desire to add/modify an entered medication, selecting the entered medication from the medication window 392 and clicking on the add/modify subject medication button 408 will allow the participant to add or modify the entered medication. If for any reason, this medication enrollment and/or intake process is not working properly or the participant must cancel from the medication process, clicking on the cancel button 410 returns the participant to the intake worksheet pane 382, as illustrated in FIG. 19. If all the medications are entered for the participant in the medications pane 390 and the list of questions 384 are completed, clicking on the done button 414 returns the participant to the intake worksheet pane 382. If all the list of questions 384 accompanied by the answer selections 386 to each of the questions 384 are completed, clicking on the done button 412 returns the participant to the add new subject pane 202, as illustrated in FIG. 7. Once complete, the enrollment process and information is now entered and the enrollment or adding of the participant into the system can be finalized. Clicking on the add subject button 238 displays a subject information pane 416, as illustrated in FIG. 21.

The subject information pane 416 redisplays the information that the participant entered for the subject id box 204, the first name box 206, the last name box 208, the dob box 210, the job classification box 212, the other classification box 214, the has fingerprint box 220, the has voice box 222, the has image box 224, the upload schedule box 216, the alternate emails section 236, the default email box 232, and the send bac fail email 234. Upon confirming that this information has been entered correctly, clicking the ok button 418 completes the enrollment process and finalizes adding the participant to the system and returns the participant to the home interface screen 168, as illustrated in FIG. 5. Once completed, proceed to Step 112.

Figure 22:
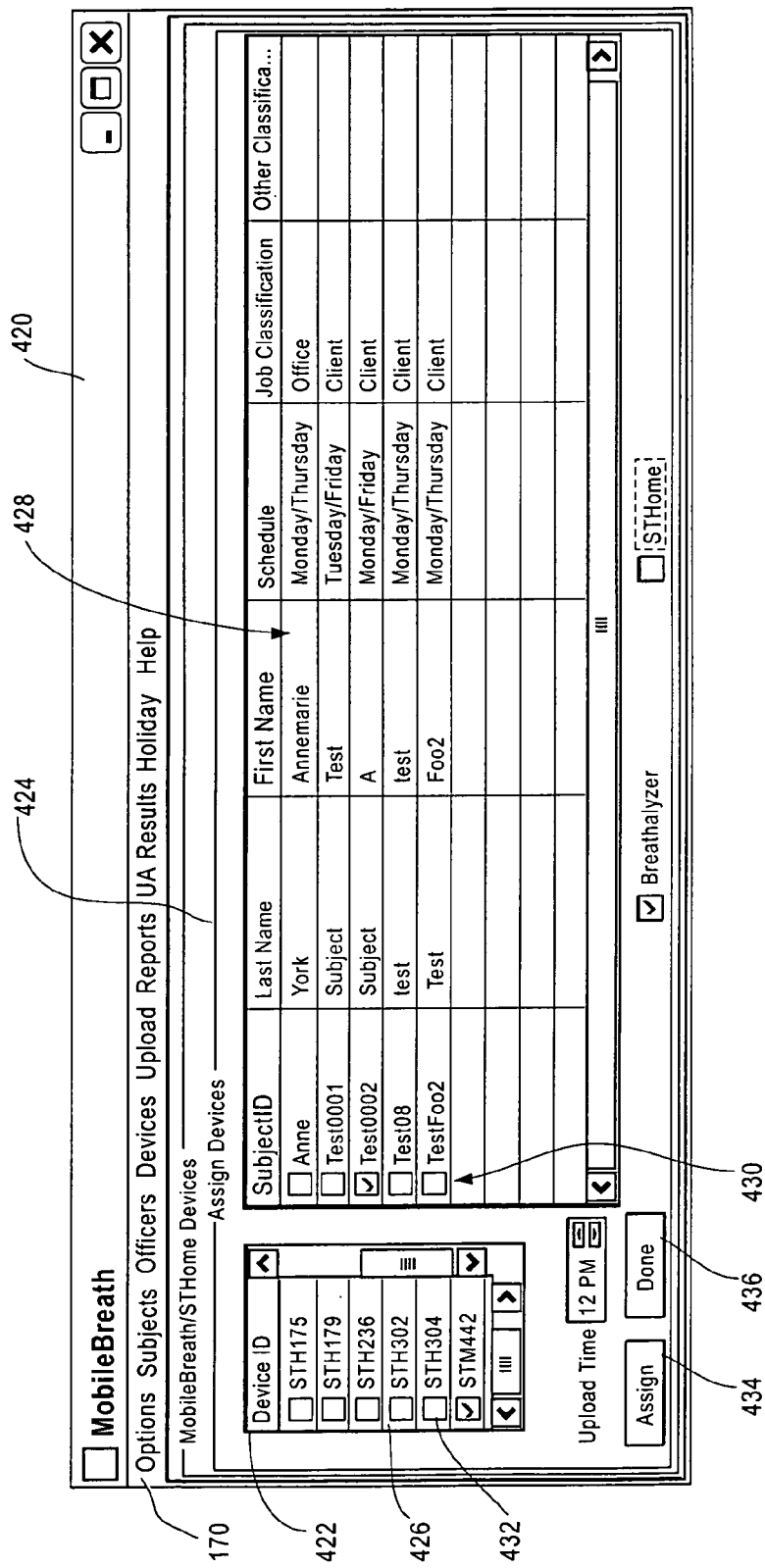
FIG. 22 is a diagram of the home devices pane resulting from the selection of the devices heading from the menu bar of the home interface screen to assign the drug testing home device to the participant.

In Step 112, once the participant has been enrolled or entered into the system, since the participant is or will be using the drug testing home device 100 to conduct their tests, a drug testing home device 100 is then assigned to the participant. Referring to home interface screen 168, as illustrated in FIG. 5, clicking on the devices heading 178 of the menu bar 170 displays the home devices pane 420, as illustrated in FIG. 22. The home devices pane 420 provides a device id section 422 and an assign devices section 424. In the preferred embodiment, the device id section 422 provides a list 426 of unassigned drug testing home devices 100 and the assign devices section 424 provides a list of participants 428 that have been enrolled into the system but have not yet been assigned a drug testing home device 100. As the participant has just been entered or enrolled into the system, the participant should be listed as part of the list of participants 428 from which the participant can place a check mark into the corresponding selection box 430. Likewise, the participant confirms the device id of the drug testing home device 100 that the participant is using for this enrollment and then places a check mark into the device selection box 432 corresponding to the appropriate drug testing home device 100. Once the participant and the drug testing home device 100 have been selected, clicking on the assign button 434 will complete the assignment of the drug testing home device 100 to the participant. Then, clicking on the done button 436 returns the participant to the home interface screen 168, as illustrated in FIG. 5.

At this point the participant may, if desired, use the menu bar 170 and proceed with configuring, altering, setting, or viewing any of the other options provided including but not limited to heading 172, subjects heading 174, officers heading 176, devices heading 178, upload heading 180, reports heading 182, UA results heading 184, holidays heading 186, and/or help heading 188. Once completed, the participant powers down the drug testing home device 100, and proceeds to Step 113.

In Step 113, the participant begins their compliance testing using the drug testing home device 100. In the preferred embodiment, the participant is to conduct their test in accordance with the fixed and random schedules previously set in the schedule pane 334, as illustrated in FIG. 16, of the enrollment process. In that non-limiting example, the first fixed test is scheduled for Sunday at 7:00 am with a grace testing period of thirty (30) minutes; the second fixed test scheduled for Sunday is at 6:00 pm with a grace testing period of thirty (30) minutes; the third fixed test scheduled for Sunday is at 11:00 pm with a grace testing period of thirty (30) minutes; and the random test scheduled in between the fixed scheduled testing for Sunday is between 11:00 am and 1:00 pm. When the first fixed test is required to be taken, the participant uses the drug testing home device 100 and boots or powers up the device. In the preferred embodiment, once the participant has enrolled into the system, the home interface screen 168 and the menu bar 170 previously used in the enrollment process are disabled to the participant.

Figure 23:
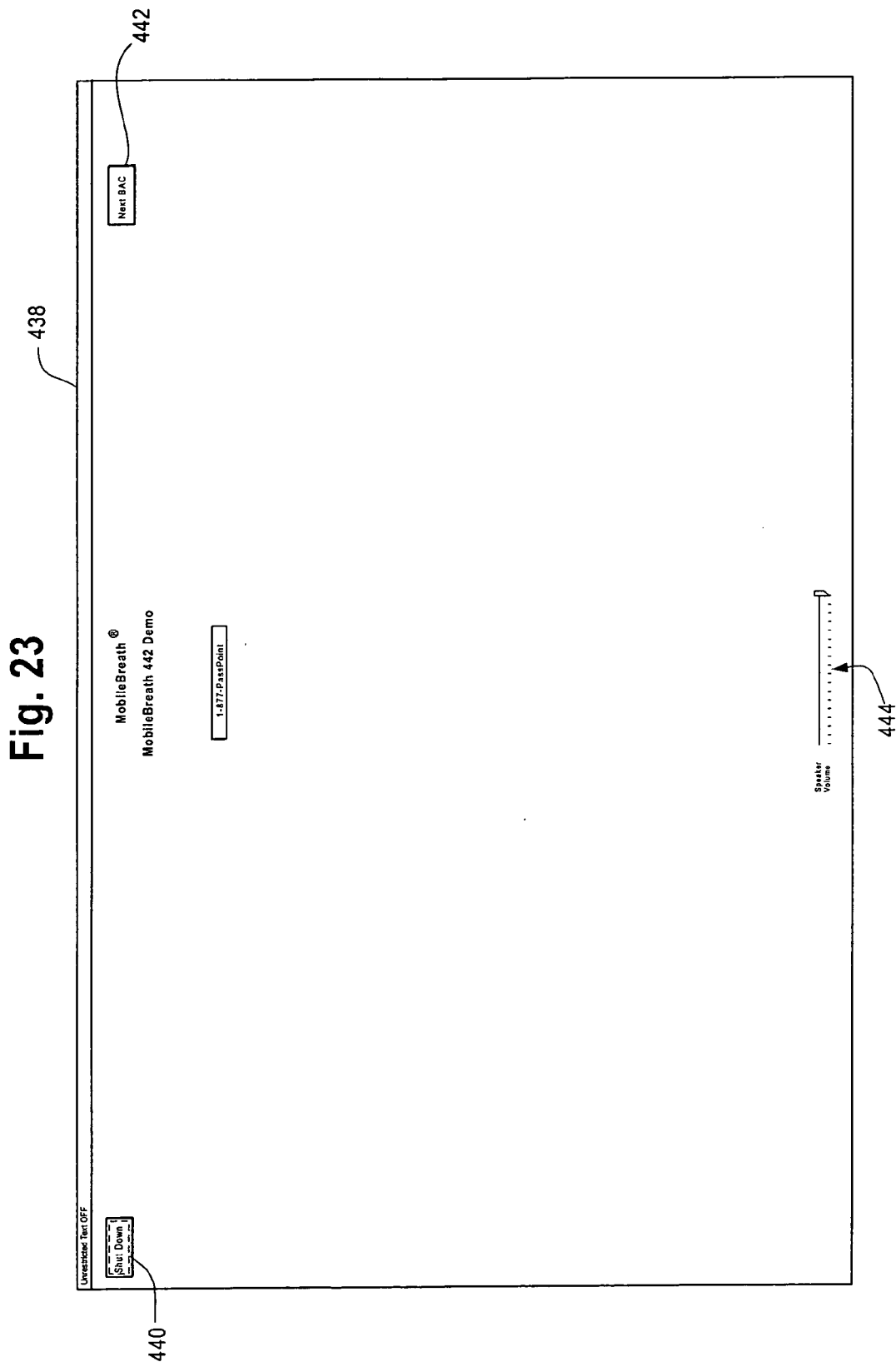
FIG. 23 is a diagram of the informational testing screen pane of the computer software for the drug testing home device.

If the participant is too early to take the test which, in the non-limiting example provided, would mean the participant is attempting to take the test on Sunday at 6:29 am or earlier (i.e., more than the 30 minutes grace period before the scheduled 7:00 am testing time), the drug testing home device 100 displays, on the lcd display screen 110 (see FIG. 1), an informational testing screen pane 438, as illustrated in FIG. 23. The informational testing screen pane 438 provides a shut down button 440, a next bac button 442, and a speaker volume setting 444 (i.e., to set the volume of the speakers to a level easily heard by the participant). If the participant realizes that they are too early for the test, clicking the shut down button 440 shuts down the drug testing home device 100. If the participant does not realize that they are too early for the test or do not happen to remember when the next scheduled test is, clicking on the next bac button 442 displays the next scheduled testing time (i.e., Sunday at 7:00 am).

Figure 24:
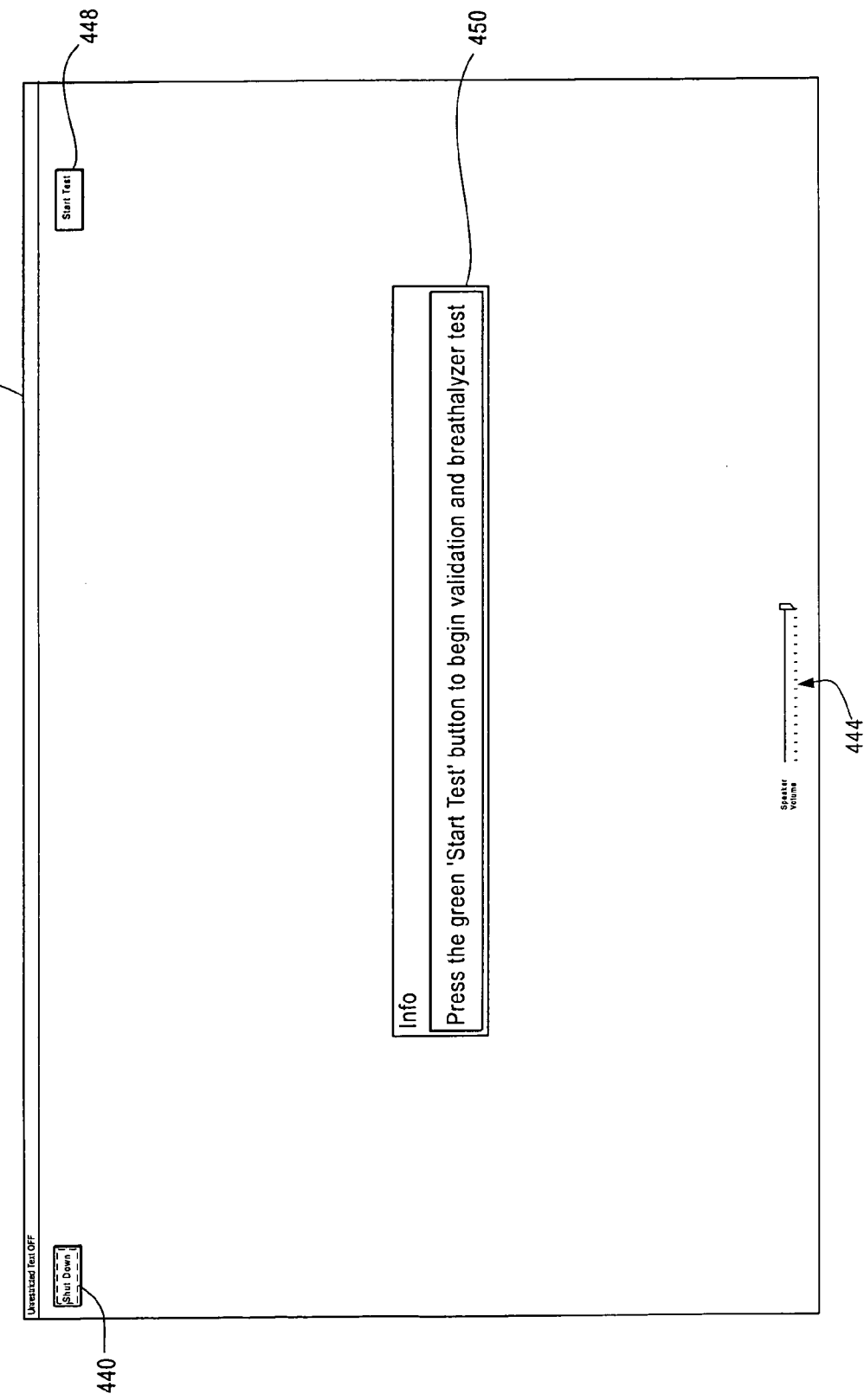
FIG. 24 is a diagram of the initial testing screen pane resulting from the selection of the next bac button from the informational testing screen pane to initiate the testing process for the participant.

If the participant is on time to take the test which, in the non-limiting example provided, would mean the participant is attempting to take the test on Sunday between 6:30 am (i.e., not more than the 30 minutes grace period before the scheduled 7:00 am testing time) and 7:30 am (i.e., not more than the 30 minutes grace period after the scheduled 7:00 am testing time), the drug testing home device 100 displays, on the lcd display screen 110 (see FIG. 1), an initial testing screen pane 446, as illustrated in FIG. 24. The initial testing screen pane 446 provides the same shut down button 440, the same speaker volume setting 444, a start test button 448, and a message display 450 which displays the message "Press the green 'Start Test' button to begin validation and breathalyzer test." To begin the testing process, the participant clicks on the start test button 448 and proceeds to Step 114.

Figure 25:
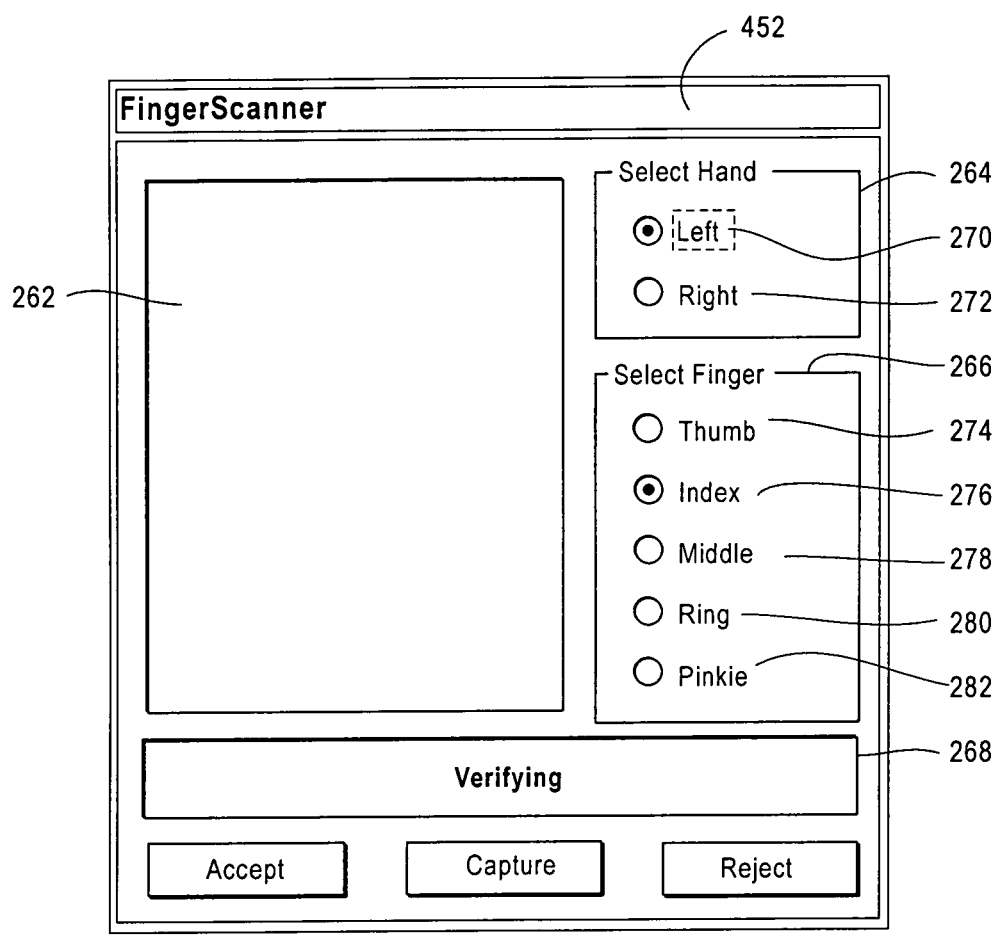
FIG. 25 is a diagram of the finger print validation pane resulting from the selection of the start test button from the initial testing screen pane to begin the validation process of the finger print biometric of the participant.

In Step 114, the biometrics of the participant taking the test are validated (also referred to as "validation process"). Upon clicking on the start test button 448 of the initial testing screen pane 446 of FIG. 24, the biometric validation process begins with a finger print validation pane 452, as illustrated in FIG. 25, to proceed to validate the finger print biometrics of the participant taking the test (also referred to as "finger print validation process"). The finger print validation pane 452 provides the finger image window 262, the select hand section 264, the select finger section 266, and the message box 268. The participant selects which hand to validate by clicking, in the select hand section 264, the left selection 270 (i.e., for the left hand) or by clicking the right selection 272 (i.e., for the right hand). In the non-limiting example provided, the left selection 270 is selected identifying the left hand. The participant then selects which finger on the selected hand to validate by clicking, in the select finger section 266, the thumb selection 274 (i.e., for the thumb finger), the index selection 276 (i.e., for the index finger), the middle selection 278 (i.e., for the middle finger), the ring selection 280 (i.e., for the ring finger), and the pinkie selection 282 (i.e., for the pinkie finger). In the non-limiting example provided, the index selection 276 is selected identifying the index finger for the left hand. The participant then places the selected finger of the selected hand in the finger print reader 114 of the drug testing home device 100. Once the hand and finger are in the finger print reader 114, the message box 268 displays the message "Verifying." If the selected finger print of the selected hand does not match the actual image 290 (see FIG. 11) of the finger print, the participant is instructed to repeat the finger print validation process again. If the selected finger print of the selected hand does not match the actual image 290 during the second attempt or again on the third attempt, the finger print validation process is failed. The test is then stopped and the participant test result is flagged as a "Missed Test." If the selected finer print of the selected hand matches the actual image 290 (see FIG. 13) of the finger print of the participant that was recorded during the finger print enrollment process, the participant's finger print is validated and passed. Once the finger print validation process is completed, proceed to the voice validation process.

To begin the voice validation process, the system audibly instructs the participant to repeat one of the suggested phrases that was recorded during the participant's voice enrollment process. In the preferred embodiment, the phrase is randomly selected from the suggested phrases that are recorded for the participant. Non-limiting examples of such phrases include but are not limited to "Have no friends not equal to yourself;" "Learning without thought is labor lost;" "Thought without learning is perilous;" "Diligence is the mother of good fortune;" etc. . . . , or any other unlimited phrases, as desired. The participant speaks the suggested phrase (also referred to as "real time phrase"). The voice recording of the participant speaking the phrase or real time phrase is then compared to the phrase of the participant that were recorded during the voice enrollment process. Alternatively, to confirm a more uniform and consistency and the possibility of a better comparison for validation purposes, the participant may be required to repeat the suggested phrase, for example, three (3) times with each real time phrase being compared to the recorded phrases enrolled into the system. If the real time phrase does not match the previously recorded phrase, the participant is instructed to repeat the voice validation process again by repeating another of the suggested phrases that was recorded during the participant's voice enrollment process. If the real time phrase does not match the previously recorded phrase during the second attempt and/or again on the third attempt, the voice validation process is failed. The test is then stopped and the participant test result is flagged as a "Missed Test." If the real time phrase matches the previously recorded phrase, the participant's voice is validated and passed. Once the voice validation process is completed, proceed to the image validation process.

In the preferred embodiment, the image validation process is performed at three intervals: the first real time image of the participant is taken during the finger print validation process, the second real time image of the participant is taken during the voice validation process, and the third real time image of the participant is taken simultaneously as the participant performs the test. In this manner, the system eliminates the possibility that the participant may attempt to pass all of the validation processes and then, before the test is conducted, have another person (i.e., not themselves) step in to perform the test to obtain a pass test result where the participant themselves may otherwise have failed.

If any one of the first real time image of the participant, the second real time image of the participant, and/or the third image of the participant, when each are individually compared to each of the facial images of the participant previously recorded during the image enrollment process, and there is no match, the image validation process is failed. The test is then stopped and the participant test result is flagged as a "Missed Test." Additionally, if the test is stopped, each of the first real time image, the second real time image, and third real time image will be uploaded to the system and optionally an email containing a link to the images will be sent to the officer or other authorized person informing them that the image validation process failed and providing the failed images in question. The officer or other authorized person would then either click an accept/refuse link or log on to the system and verify whether the images are, in fact, correct and of the participant or whether the images are not of the participant and, in fact, of a different person. If the officer verifies that the images are of the participant, these images are then purged from the system. If the officer does not or cannot verify that the images are of the participant or of a different person, the officer may print the pictures for their file and subsequent investigation. Preferably, the system will then maintain these images for thirty (30) days. There will be a report that shows all unverified image validations in the last forty-eight (48) hours. After forty-eight (48) hours, any unverified images will be deleted from the system.

If all of the first real time image of the participant, the second real time image of the participant, and the third image of the participant, when compared, each match the previously recorded facial images of the participant, the participant's image is validated and passed. Once the image validation process is completed, proceed to Step 115.

In Step 115, the test is completed and results are analyzed. As previously described, while the third real time image of the participant is being taken for the image validation process, the participant is simultaneously performing the test. To perform the test, the participant inserts a straw 454 into a blow hole 456 of the drug testing home device 100, as illustrated in FIG. 1, which is in direct communication with the breathalyzer device 118. The participant is instructed to and blows firmly into the straw 454 until a beep is sound. Upon hearing the beep sound, the participant can then stop blowing. The breathalyzer device 118 analyzes the contents of the air blown into the breathalyzer device 118 from the participant. In the preferred embodiment, the breathalyzer device 118 analyzes the blood alcohol content (also referred to as bac level). Blood alcohol content is the amount of alcohol present in a 100 milliliter (mL) volume of blood based on the air blown into the breathalyzer device 118. For example 80 mg is 0.08 grams, 0.08 grams of alcohol in 100 mLs is written as 0.08%. In other words, 80 mg % is equal to 0.08% which is equal to 80 mg/dL (deciliter; 100 mLs). This value can also be described as 0.08 BAC. If the blood alcohol level is determined to be equal to zero (0), the participant has successfully passed the test. Once the test is passed, proceed to Step 117. If the blood alcohol level is determined to be greater than zero (0), the participant has failed the test, proceed to Step 116.

Alternatively, should the multi-testing device 118, as described above and illustrated in FIGS. 43(A)-(F), be used instead of the breathalyzer device 118, the test of the participant's blow into the multi-testing device 118 would include the breathalyzer or ethanol sensor 540 to test for the presence of alcohol and the Volatile Organic Compound (VOC) sensor 542 and pH sensor 544 to test for the presence of drugs.

If the blood alcohol level is determined, from the reading by the breathalyzer or ethanol sensor 540, to be equal to zero (0), the participant has successfully passed the breathalyzer or ethanol test. If the blood alcohol level is determined to be greater than zero (0), the participant has failed the test.

The gas reading from the Volatile Organic Compound (VOC) sensor 542 (also referred to as "real time voc reading") is compared to the Volatile Organic Compound (VOC) readings recorded during the participant's voc enrollment process. If the real time voc reading is greater than (i.e., >) the Volatile Organic Compound (VOC) reading recorded during the participant's voc enrollment process, the participant is instructed to repeat the voc validation process again. If the gas reading from the Volatile Organic Compound (VOC) sensor 542 (i.e., real time voc reading) remains greater than (i.e., >) the Volatile Organic Compound (VOC) reading recorded during the participant's voc enrollment process during the second attempt or again on the third attempt, the Volatile Organic Compound (VOC) validation process is failed. If the gas reading from the Volatile Organic Compound (VOC) sensor 542 (i.e., real time voc reading) is less than or equal to (i.e, ≦) the Volatile Organic Compound (VOC) reading that was recorded during the voc enrollment process of the participant, the participant's voc is validated and passed.

If the acidity reading from the pH sensor 544 (also referred to as "real time pH reading") is compared to the pH readings recorded during the participant's pH enrollment process. If the real time pH reading is greater than (i.e., >) the pH reading recorded during the participant's pH enrollment process, the participant is instructed to repeat the pH validation process again. If the acidity reading from the pH sensor 544 (i.e., real time pH reading) remains greater than (i.e., >) the pH reading recorded during the participant's pH enrollment process during the second attempt or again on the third attempt, the pH validation process is failed. If the acidity reading from the pH sensor 544 (i.e., real time pH reading) is less than or equal to (i.e., <) the pH reading that was recorded during the pH enrollment process of the participant, the participant's pH is validated and passed.

Based on the test results, the participant is determined to have failed the test if any of the results fall within the following conditions or criteria: (i) if the breathalyzer or ethanol test is a fail; (ii) if the breathalyzer or ethanol test is a pass, the voc test is a fail, and the pH test is a pass; and (iii) if the breathalyzer or ethanol test is a pass, the voc test is a fail, and the pH test is a fail. Once the test is completed and if the participant failed the test, the participant is instructed to contact their supervisor or other authorized person and advise them of the results of the failed test to receive further instructions from the supervisor or other authorized person such as being subjected to a urinalysis exam which should include testing for including but not limited to alcohol, THC, cocaine, methamphetamine, opiates, etc. . . . . Also, once the test is completed and the participant has failed the test, proceed to Step 117.

Based on the test results, the participant is determined to have successfully passed the test if any of the results fall within the following conditions or criteria: (i) if the breathalyzer or ethanol test is a pass, the voc test is a pass, and the pH test is a pass; and (iii) if the breathalyzer or ethanol test is a pass, the voc test is a pass, and the pH test is a fail. Once the test is completed and the participant has successfully passed the test, proceed to Step 117.

In Step 116, if the participant fails the test, the system instructs the participant to repeat the test in fifteen (15) minutes and then prior to the participant repeating the test, the system conducts a contamination test. The contamination test is a test to determine if the straw 454 is contaminated and therefore causing the unsuccessful or failed test. While the participant waits to repeat the test in fifteen (15) minutes, the system, using the breathalyzer device 188, performs another test with the straw 454 that remains connected or inserted into the blow hole 456 of the drug testing home device 100, as illustrated in FIG. 1, except this time there is no air being blown through the straw 454 from the participant. Instead, the system performs the test on the air that is contained within the straw 454 only. If the blood alcohol level is determined to be equal to zero (0), the straw 454 is not contaminated and the system will instruct the participant to repeat the test at the fifteen (15) minute time frame. If the blood alcohol level is determined to be greater than zero (0), the straw 454 is contaminated and the system will instruct the participant to replace the straw 454 with a new straw 454 and then repeat the test at the fifteen (15) minute time frame. If the participant fails the repeat test, the participant is instructed to contact their supervisor or other authorized person and advise them of the results of the failed test to receive further instructions from the supervisor or other authorized person such as being subjected to a urinalysis exam. The participant is then instructed to shut down or turn off the drug testing home device 100. If the participant passes the repeat test, the participant is instructed to shut down or turn off the drug testing home device 100. Once the test is completed and the participant has either successfully passed the test or failed the test, proceed to Step 117.

In Step 117, notification of the test results are sent to all the interested persons. In the preferred embodiment, all of the persons identified or provided in the alternate emails section 236, the send default email box 232, and/or the send bac fail email 234 (each provided in the add new subject pane 202 as illustrated in FIG. 7) including but not limited to particular officer(s) responsible for the participant or other person(s) such as a supervising officer, regular officer, treatment person, judge, or any other person interested in and authorized to receive the testing information of the participant will receive a notification of the test results to their e-mail. In the preferred embodiment, if the participant successfully passed the test, the pass email, as illustrated in FIG. 31, will be sent. If the participant was unsuccessful or failed the test, the failed email, as illustrated in FIG. 32, will be sent. Other notifications during the testing process also include the following. If the participant does not conduct the test when required, the test not taken email, as illustrated in FIG. 33, will be sent. If the participant begins a test but does not complete the test, the test incomplete—fault email, as illustrated in FIG. 34, will be sent. If the participant begins a test but fails the validation process, the validation failed email, as illustrated in FIG. 35, will be sent. If the participant begins a test but initially fails the test (i.e., prior to the subsequent contamination process), the evidentiary email, as illustrated in FIG. 36, will be sent. Other notifications during the testing schedule include the following. If the participant has not conducted many tests when required (i.e., has missed their schedule testing times many times over the course of the schedule), the missed test email, as illustrated in FIG. 37, and the missed bac report, as illustrated in FIG. 38, will be sent. Additionally, validation request emails, as illustrated in FIG. 39, and bac activity reports, as illustrated in FIG. 40, are also available.

Once this testing process is completed, the participant proceeds back to Step 113 and repeats the process for each subsequent scheduled testing.

Figure 26:
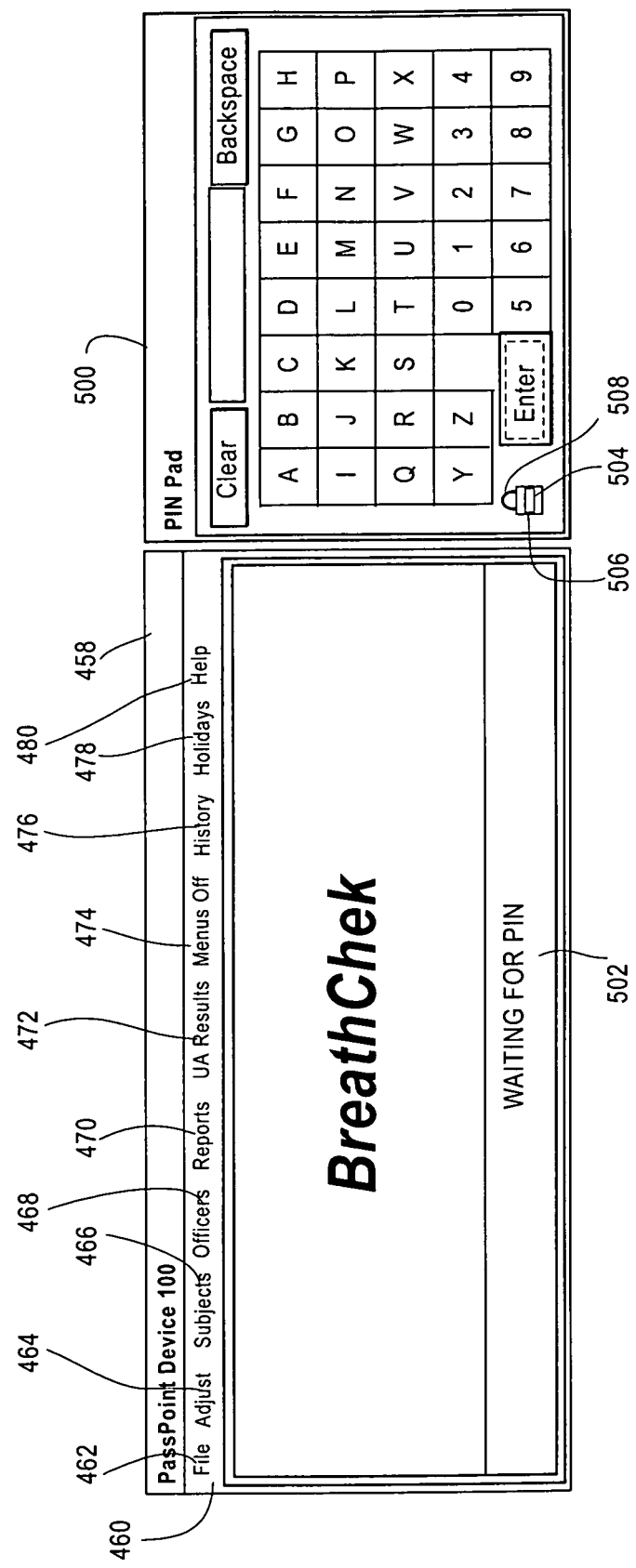
FIG. 26 is a diagram of the kiosk interface screen pane of the computer software for the drug testing kiosk device.

In Step 118, if the participant is already entered or enrolled into the computer system, proceed to conducting the test, as described in further detail below. If the participant is not entered or enrolled into the computer system, proceed to enroll the participant into the system using the enrollment process. The drug testing kiosk device 102 provides a kiosk interface screen 458, as illustrated in FIG. 26, on the lcd display screen 110. The kiosk interface screen 458 also provides a message box 502 and an interactive pin pad 500. Initially, the message box 502 displays the message "Waiting for Pin." The pin pad 500 provides a lock 504 which displays a base 506 and a hook 508. As illustrated, lock 504 is shown in the locked configuration with the hook 508 shown as closed within the base 506. In this manner, the kiosk interface screen 458 remains disabled to the participant until the lock 504 is opened. To open the lock 504, the supervisor or other authorized person for the participant clicks on the lock 504 and then enters an authorized pin number into the pin pad 500. Upon the system accepting the authorized pin number, the lock 504 becomes opened (i.e., one end of the hook 508 rotates 180° degrees away from the base 506 to show that the lock 504 is currently opened) and the kiosk interface screen 458 becomes enabled to the participant. The participant can now proceed to enroll into the system.

The kiosk interface screen 458 comprises a menu bar 460 which provides access to all of the options of the kiosk interface screen 458. The menu bar 460 provides a file heading 462, an adjust heading 464, a subjects heading 466, an officers heading 468, a reports heading 470, a UA results heading 472, a menus off heading 474, a history heading 476, a holidays heading 478, and a help heading 480.

Figure 27:
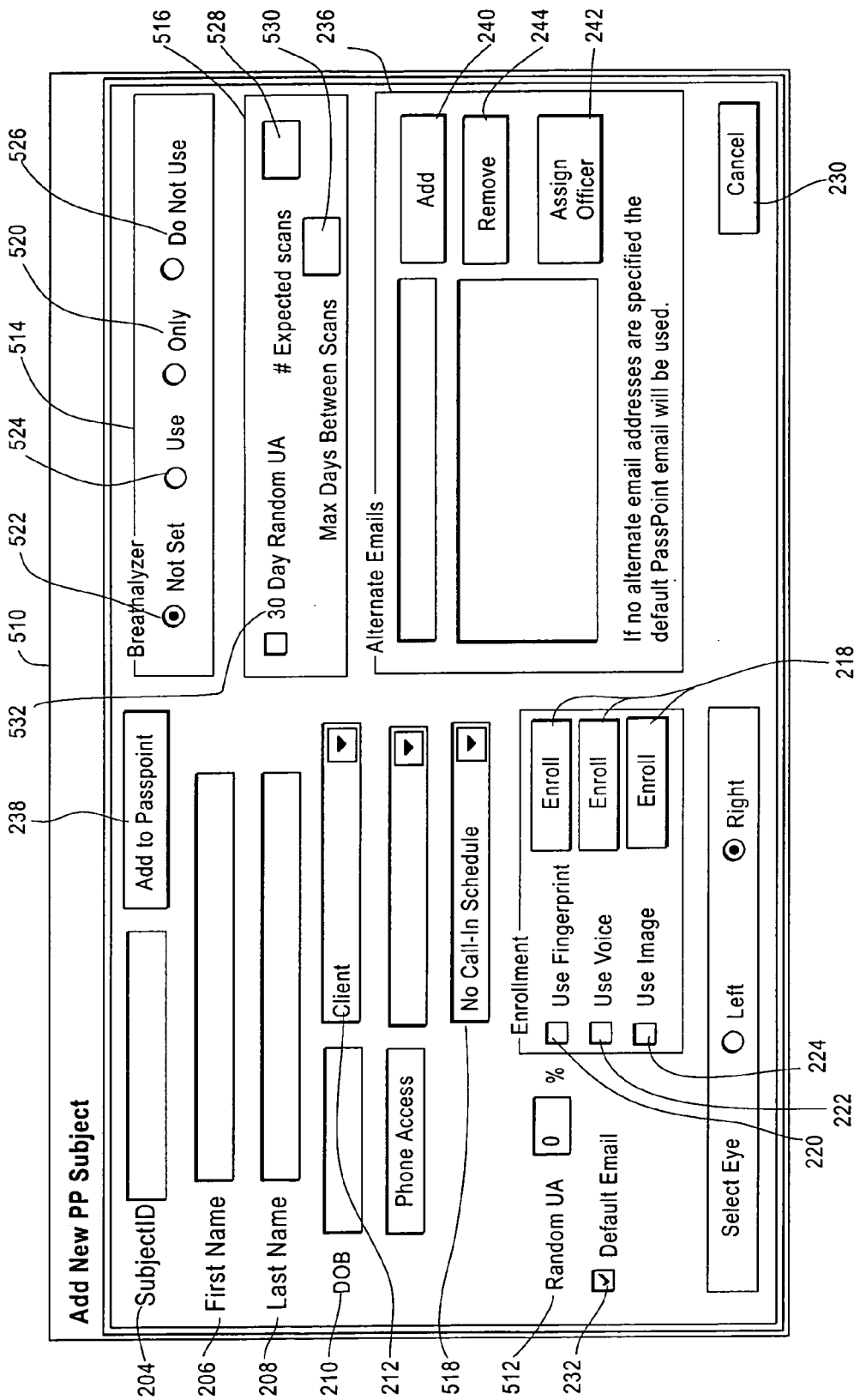
FIG. 27 is a diagram of the add new subject pane resulting from the selection of the subjects heading from the menu bar of the kiosk interface screen.

Using the menu bar 460, the subjects heading 466 is selected, by touching the lcd display screen 110 of the drug testing kiosk device 102 using their finger or other pointing device. The subjects heading 466 displays a drop down menu to add a new subject which, upon selecting, provides an add new subject pane 510, as illustrated in FIG. 27. This process may be designated by the nomenclature of "Subjects>Add New Subject". The "Subject" refers to the subjects heading 466 and the "Add New Subject" refers to the option on the drop down menu. Alternatively, it is contemplated that this process of accessing the add new subject pane 510 may be loaded using a toolbar icon (not illustrated) which provides an icon to select to accomplish this same step.

In FIG. 27, the add new subject pane 510 provides the information to enroll the participant into the system. In the preferred embodiment, the process to enroll a participant into the system using the drug testing kiosk device 102 is nearly identical to the enrollment process using the drug testing home device 100 as previously described in Steps 105 through Step 110.

In this manner, the add new subject pane 510 accomplishes the enrollment process with the same information from the subject id box 204, the first name box 206, the last name box 208, the dob box 210, the job classification box 212, the enroll button 218, the has fingerprint box 220, the has voice box 222, the has image box 224, the cancel button 230, the send default email box 232, the alternate emails section 236, and the add subject button 238. In the preferred embodiment, the enrollment process relating to each of these is identical to the enrollment process using the drug testing home device 100 as previously described in Steps 105 through Step 110.

As the drug testing kiosk device 102 is a publicly accessible device that is designed to be used by many participants and not just one participant like the drug testing home device 100 which is individually assigned to each participant, the drug testing kiosk device 102 also requires additional information to complete the enrollment process relating to Step 106.

In addition to performing the same steps as previously described in Step 106, the enrollment process for the drug testing kiosk device 102 also provides for the completion of the following information which includes but is not limited to a breathalyzer setting 514, a test setting 516, a random ua setting 512, and a call-in setting 518. Each are discussed in further detail below.

The breathalyzer setting 514 allows the participant to identify which system of the drug testing kiosk device 102 is being used. In the preferred embodiment, the drug testing kiosk device 102 uses the breathalyzer or multi-testing device 118, as illustrated in FIGS. 2 and 3. Clicking on the only selection 520 confirms the use of only the breathalyzer or multi-testing device 118. Alternatively, the drug testing kiosk device 102 may be provided with eye-scanning devices (not illustrated). If so, clicking on either the not set selection 522 or use selection 524 confirms that the drug testing kiosk device 102 is equipped with both the breathalyzer or multi-testing device 118 and an eye-scanning device (not illustrated) for combined use in testing the participant. Should the drug testing kiosk device 102 only use the eye-scanning device to test the participant and not include the breathalyzer or multi-testing device 118, clicking on the do not use selection 526 confirms that use.

The test setting 516 allows the supervisor or other authorized person of the participant to set the testing schedule for the participant. In the preferred embodiment, setting the testing schedule for the drug testing kiosk device 102 accomplishes the same as Step 110 for the drug testing home device 100, except that the enrollment process in conducting this Step 110 for the drug testing kiosk device 102 is slightly different. As the drug testing kiosk device 102 is not as convenient as the drug testing home device 100 and therefore not as easily accessible or useable by the participants, the testing schedule for a participant using the drug testing kiosk device 102 may be less frequent than the schedule set for the participant using the drug testing home device 100. In this manner, the participant using the drug testing kiosk device 102 may also be required to be subjected to scheduled or random urinalysis tests as described in further detail below.

The test setting 516 provides a number of expected scans 528, a max days between scans 530, and a 30 day random selection 532. The number of expected scans 528 represents the total number of times that the participant is to be tested in a given time frame such as per day, per week, and/or per month. Preferably, the time frame is per month. The max days between scans 530 represents the maximum number of days that can elapse between each test. For participants that require frequent testing, this max days between scans 530 may be a smaller number such as any days less than five (5) days between tests. For participants that do not require as much testing, the max days between scans 530 may be a larger number such as any days more than five (5) days between tests. In the preferred embodiment, the call-in setting 518 identifies whether the participant can call in to obtain their schedule or not. And, this call-in setting 518 is highlighted in a particular color such as green, blue, red, yellow, or any color known to one skilled in the art. The color assigned to the call-in setting 518 also represents or corresponds to the max days between scans 530 and the frequency that the participant is required to be tested.

The 30 day random selection 532 and random ua setting 512 represent the frequency that the participant is required to undergo a urinalysis testing exam. The 30 day random selection 532, if selected, means that the participant, independent of the number of expected scans 528, is required to undergo a urinalysis testing exam at least once within every thirty (30) days. The random ua setting 512 represents the percentage or number of times that the participant is required to undergo a urinalysis testing exam in proportion to the total number of expected scans 528. For example, if the random ua setting 512 is 20, this would mean that 20% of the time, the participant would be required to undergo a urinalysis testing exam. If the total number of expected scans 528 is 100 per month, in this non-limiting example, the participant would be required to under a urinalysis testing exam 20% of 100 or one (1) out of every five (5) tests.

Figure 28:
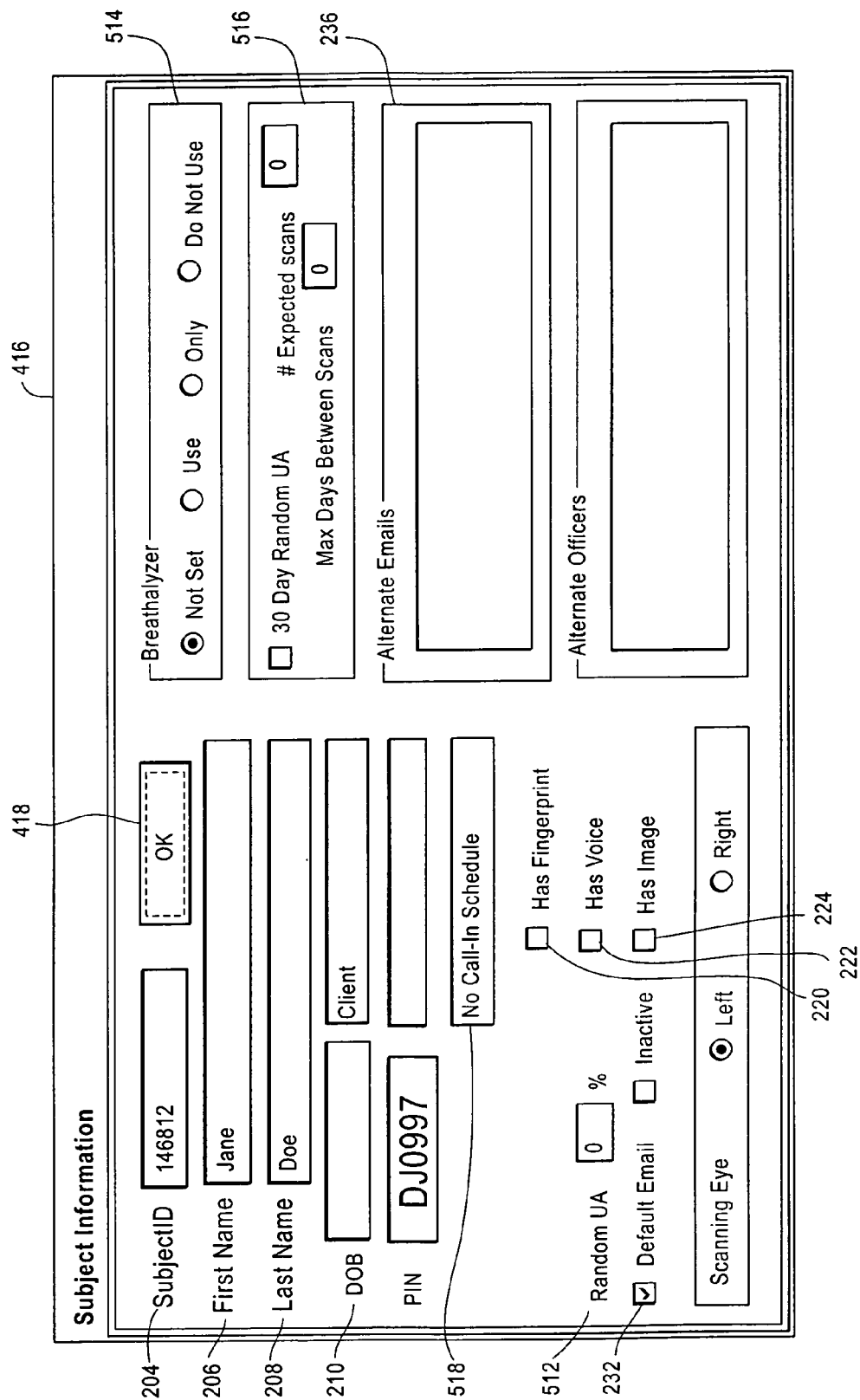
FIG. 28 is a diagram of the subject information pane resulting from the selection of the add subject button from the add new subject pane to complete the enrollment of the participant into the system using the drug testing kiosk device.

Once the enrollment process for adding or enrolling the participant into the system is complete, clicking on the add subject button 238 displays a subject information pane 416, as illustrated in FIG. 28. The subject information pane 416 then redisplays much of the information that the participant entered into the add new subject pane 510. Upon confirming that this information has been entered correctly, clicking the ok button 418 completes and finalizes enrolling the participant into the system and returns the participant to the kiosk interface screen 458, as illustrated in FIG. 26.

At this point the participant may, if desired, use the menu bar 460 and proceed with configuring, altering, setting, or viewing any of the other options provided including but not limited to the file heading 462, the adjust heading 464, the subjects heading 466, the officers heading 468, the reports heading 470, the UA results heading 472, the menus off heading 474, the history heading 476, the holidays heading 478, and the help heading 480. Once completed, the participant powers down the drug testing kiosk device 102, and, then when scheduled testing is to be conducted, proceeds to the testing process.

Figure 29:
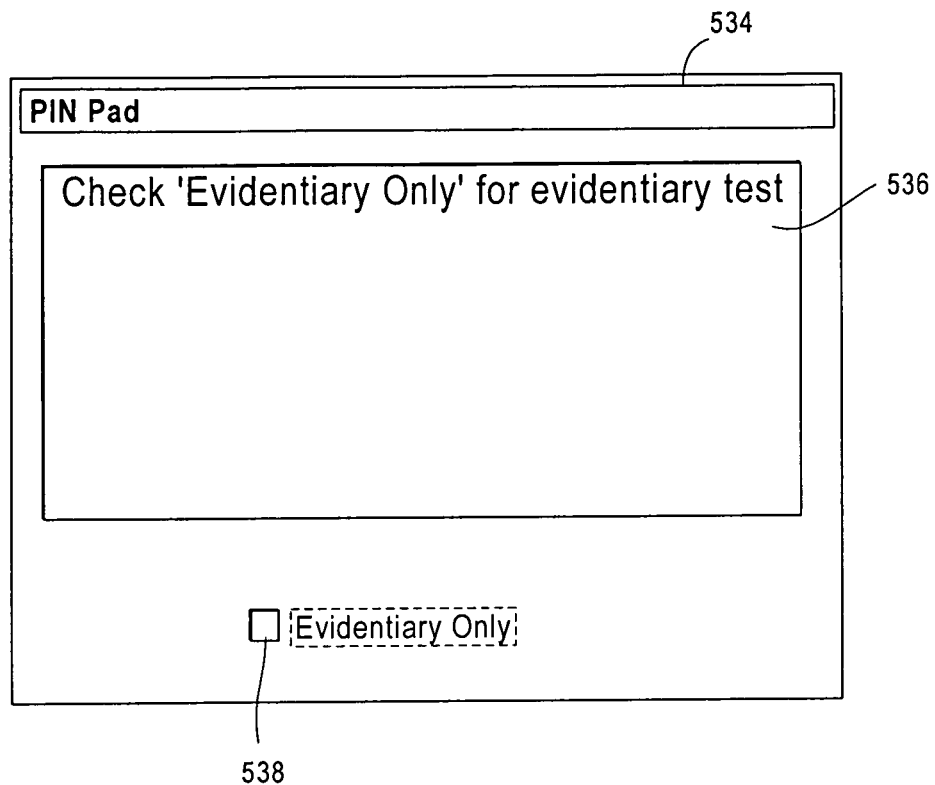
FIG. 29 is a diagram of the evidentiary test pane during the testing process using the drug testing kiosk device.

In the preferred embodiment, the testing process of the participant using the drug testing kiosk device 102 is nearly identical to the testing process using the drug testing home device 100 as previously described in Step 113 through Step 116. In addition to performing the same steps as previously described in Step 113 through Step 116, the testing process for the drug testing kiosk device 102 also provides the option of selecting between conducting the test by inserting the straw 454 into the breathalyzer hole 166 of the breathalyzer or multi-testing device 118 and blowing through the straw 454 or, alternatively, blowing directly into the breathalyzer hole 166 of the breathalyzer or multi-testing device 118. To select between these options, during the testing process, an evidentiary test pane 534, as illustrated in FIG. 29, is displayed. The evidentiary test pane 534 provides a message window 536 and an evidentiary only selection 538. Initially, the message window 536 displays the message "Check 'Evidentiary Only' for evidentiary test." If the participant selects the evidentiary only selection 538 by placing a check mark to make this selection, the participant is selecting to conduct the test using the straw 454. If the participant does not select the evidentiary only selection 538 and does not place a check mark to make this selection (i.e., leaving the evidentiary only selection 538 blank), the participant is selecting to conduct the test without the straw 454 (i.e., blow directly into the breathalyzer hole 166 instead). Should the participant likewise remain at this evidentiary test pane 534 for too long (i.e., a certain time frame such as five (5) minutes or more) without making a selection, the system shall proceed with the test without the straw 454. Should the participant place a check mark into the evidentiary only selection 538 to make this selection, the participant is selecting to conduct the test using the straw 454 and, upon doing so, shall perform the test and analysis in the same manner with the breathalyzer or multi-testing device 118 as described in Step 113 through Step 116.

Figure 30:
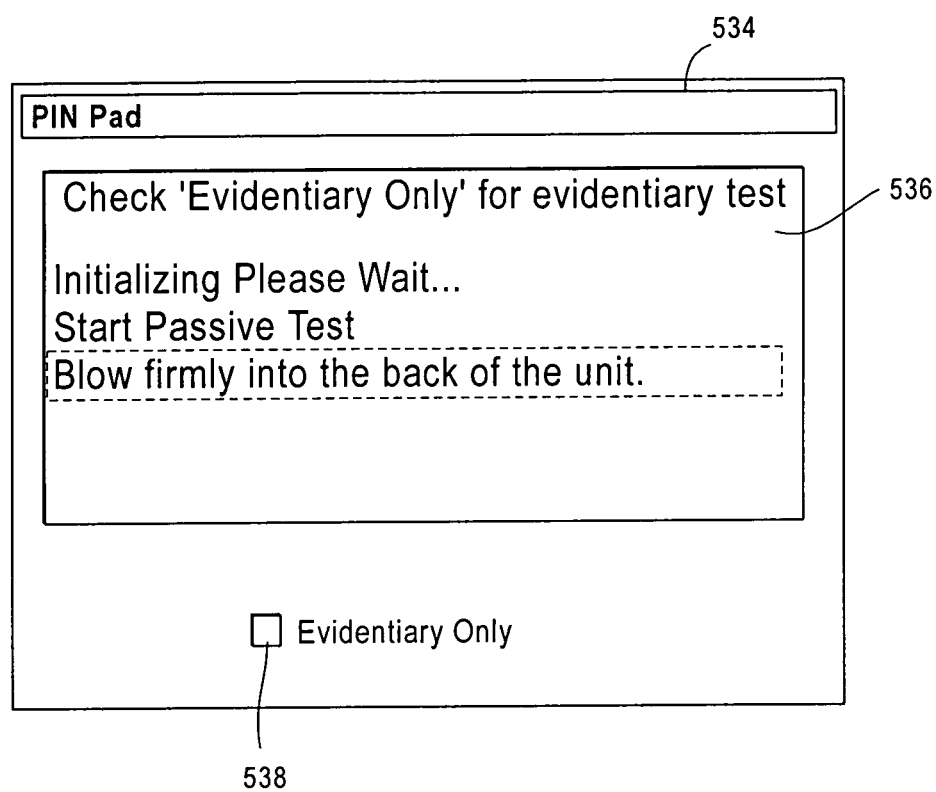
FIG. 30 is a diagram of the evidentiary test pane continuing the testing process using the drug testing kiosk device.
Figure 43A:
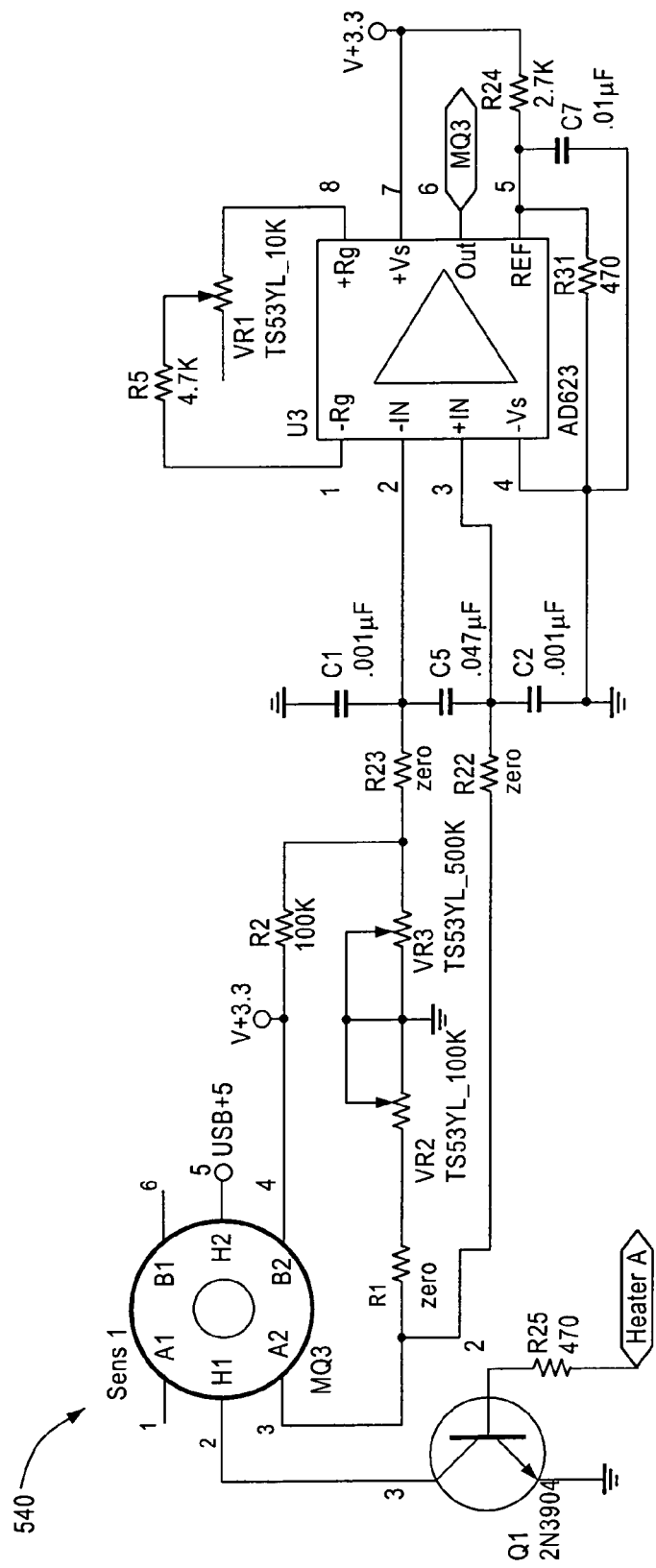
FIG. 43(A) is an electrical schematic or circuit board diagram of the multi-testing device to test for breathalyzer or ethanol using either the drug testing home device and/or the drug testing kiosk device.
Figure 43B:
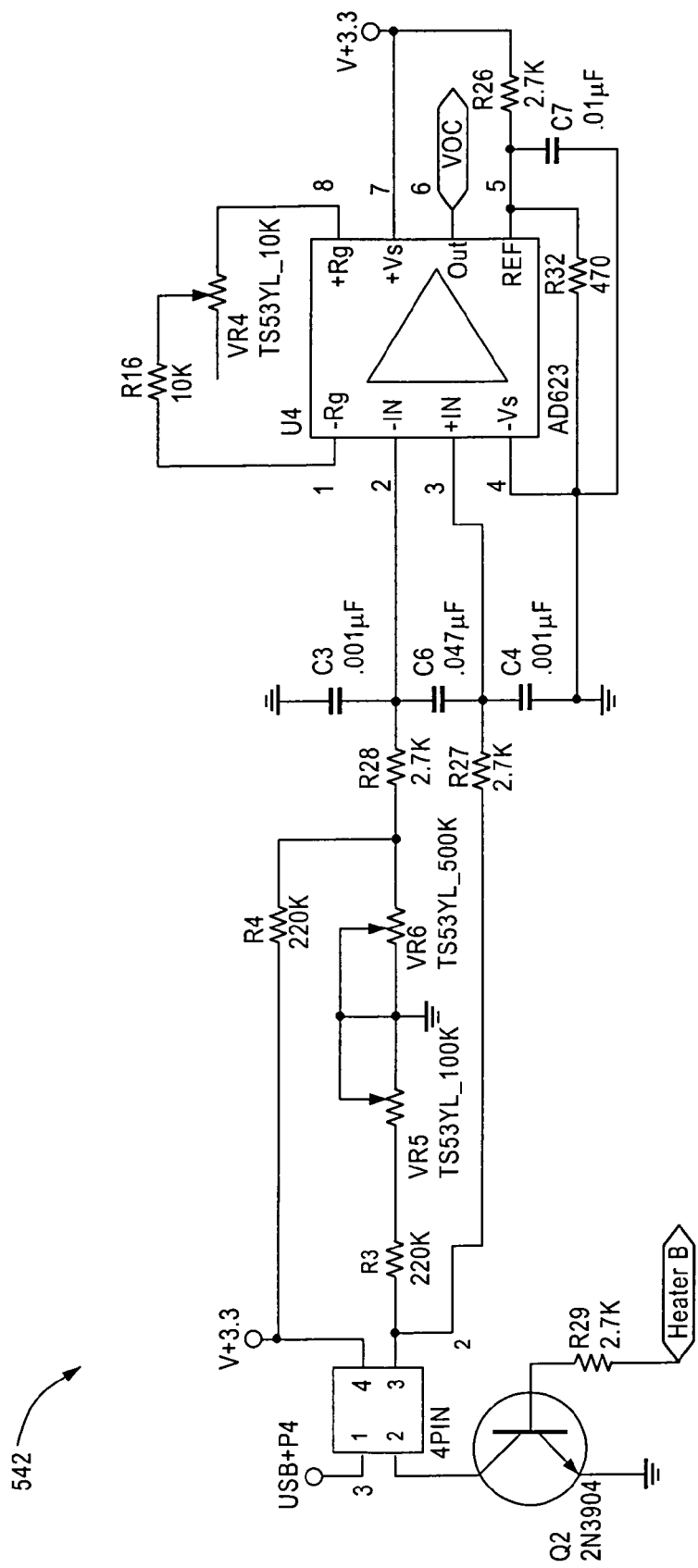
FIG. 43(B) is an electrical schematic or circuit board diagram of the multi-testing device to test for volatile organic compound (voc) gas levels using either the drug testing home device and/or the drug testing kiosk device.
Figure 43C:
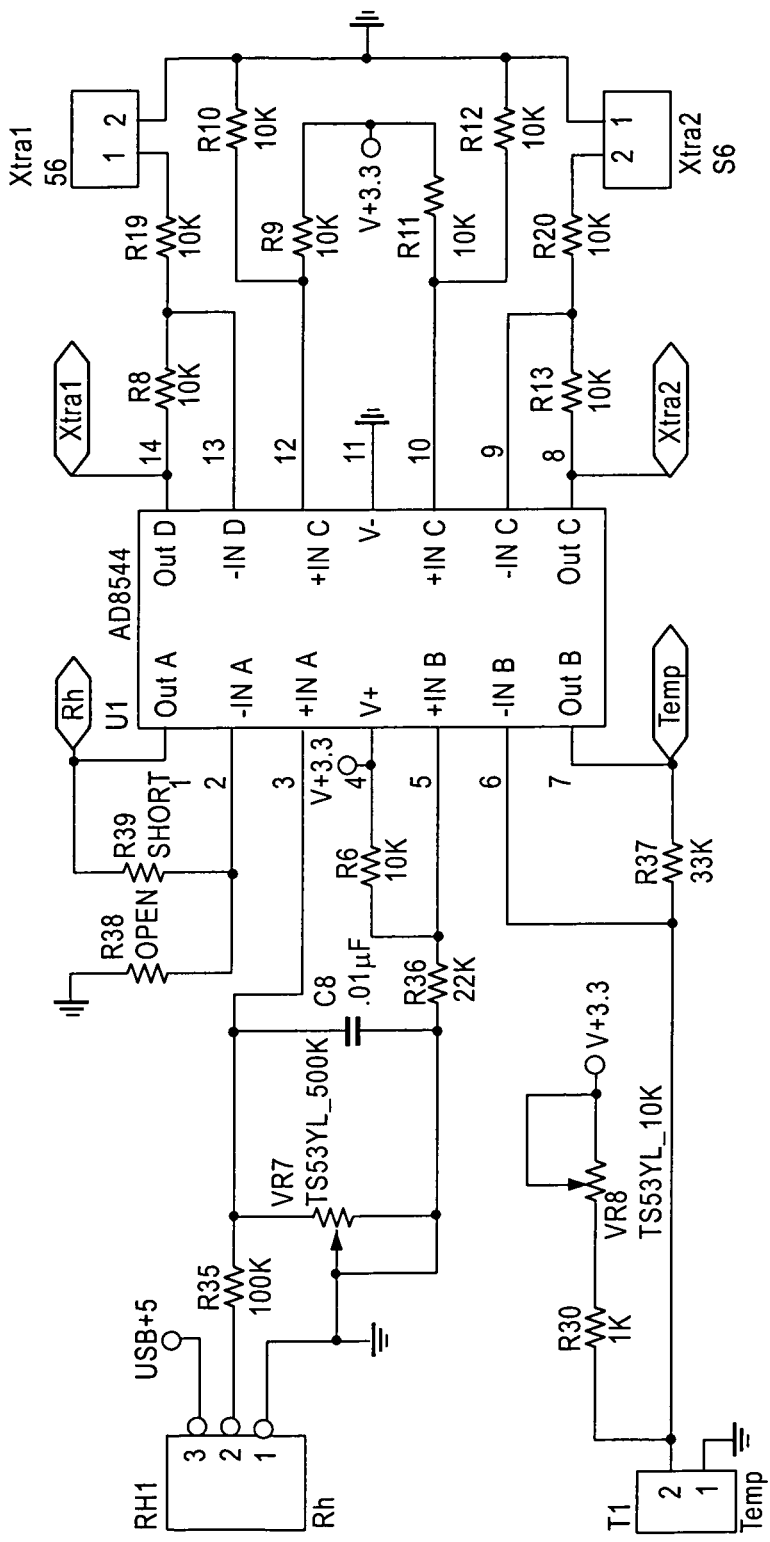
FIG. 43(C) is an electrical schematic or circuit board diagram of the multi-testing device to test for pH levels using either the drug testing home device and/or the drug testing kiosk device.
Figure 43D:
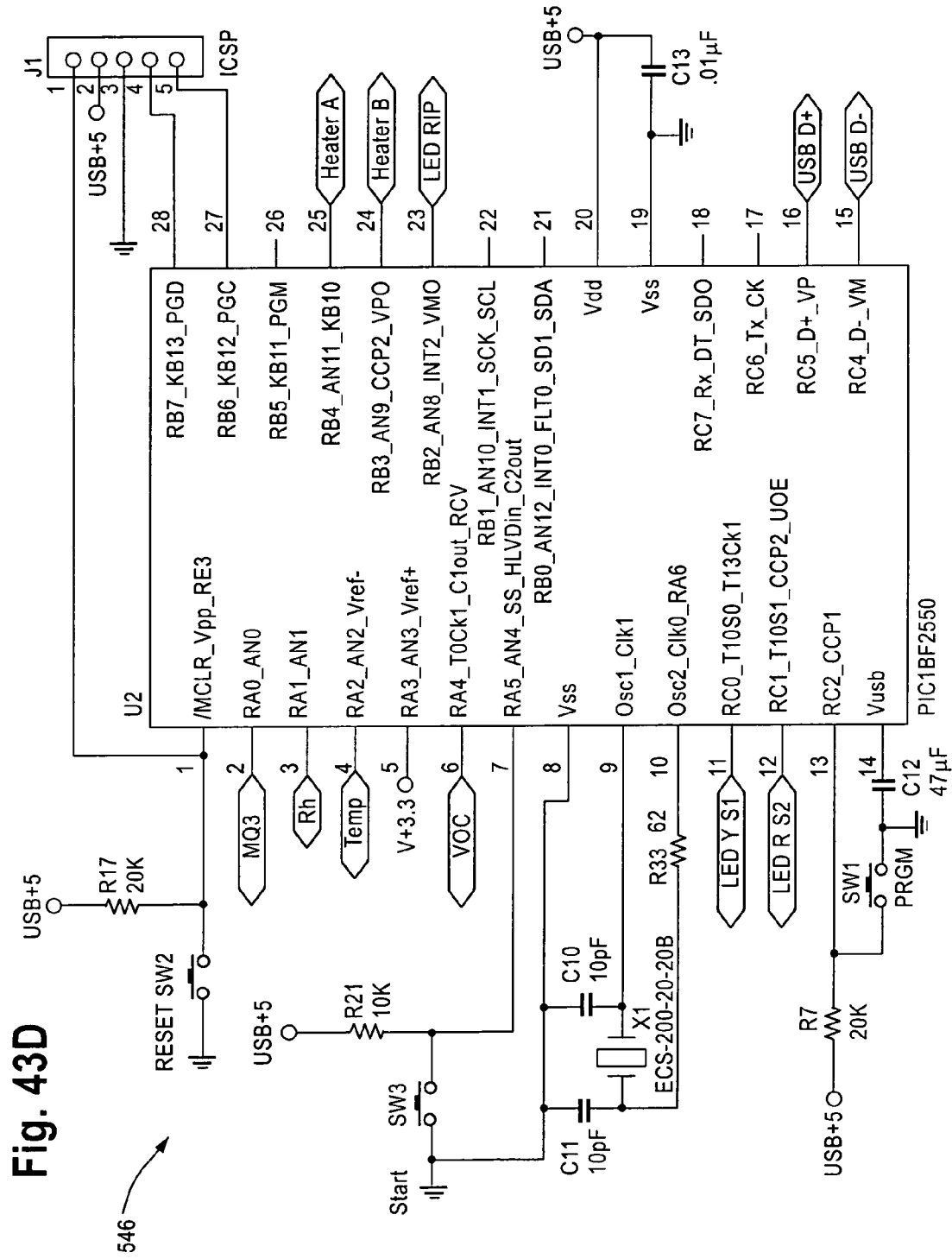
FIG. 43(D) is an electrical schematic or circuit board diagram of the connection of the multi-testing device to test for breathalyzer or ethanol, volatile organic compound (voc) gas levels, and/or pH levels with either the drug testing home device and/or the drug testing kiosk device.
Figure 43F:
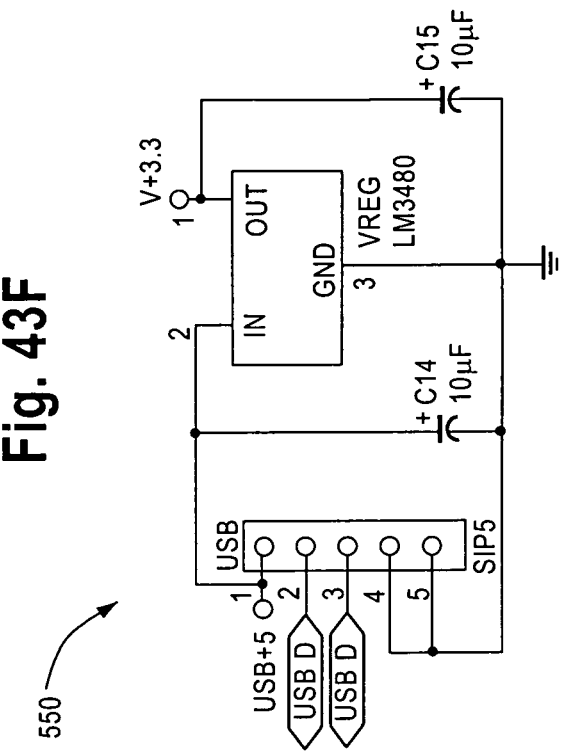
FIG. 43(F) is an electrical schematic or circuit board diagram of an additional circuit for use with either the drug testing home device and/or the drug testing kiosk device.
Figure 43E:
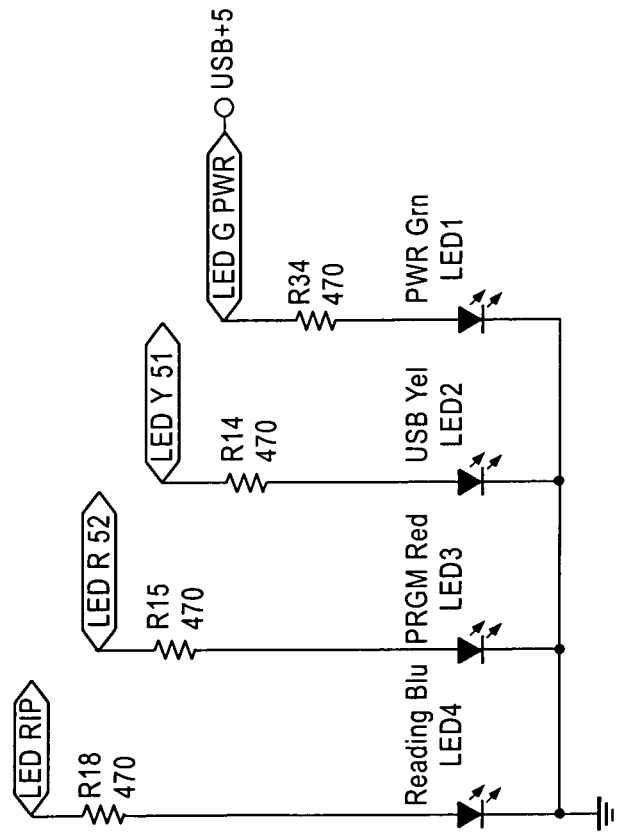
FIG. 43(E) is an electrical schematic or circuit board diagram of an additional circuit for use with either the drug testing home device and/or the drug testing kiosk device.

Upon selecting to conduct the test without the straw 454 (i.e., blow directly into the breathalyzer hole 166), the message window 536 of the evidentiary test pane 534 displays the message "Check 'Evidentiary Only' for evidentiary test . . . Initializing Please Wait . . . Start Passive Test . . . Blow firmly into the back of the unit," as illustrated in FIG. 30. The analysis of this test is performed in a slightly different manner than as described with the breathalyzer device 118 in Step 115. The reason for the difference is that, as the participant is blowing directly into the breathalyzer hole 166, there is a possibility that the participant may try varying blowing techniques (i.e, blowing too hard into the breathalyzer hole 166, blowing at various angles into the breathalyzer hole 166, blowing too softly into the breathalyzer hole 166, et. . . . ) all in an effort to circumvent or avoid an unsuccessful failed test or to develop a method to always achieve a successful pass test even in circumstances when the participant knows that they have been or are taking alcohol and/or drugs in violation of their probation or treatment. To alleviate any improper tampering with this test, the following steps applying certain rules or criteria are conducted to analyze whether the blow from the participant is acceptable or not acceptable to continue the testing process.

The participant is required to blow directly into the breathalyzer hole 166 of the breathalyzer or multi-testing device 118 (also referred to as "real time blow"). In this manner, the participant's blow is also then directly engaging the microphone 164 (see FIG. 2) of the breathalyzer or multi-testing device 118.

In the preferred embodiment, the system is provided with a database of blow sounds (i.e., .wav file) that are acceptable and blow sounds that are not acceptable (also referred to as "previously stored acceptable blow sounds and/or unacceptable blow sounds"). In the preferred embodiment, each acceptable and/or unacceptable blow sound have a pulse-code modulation (i.e., PCM) signature. The PCM signature represents a digital representation of an analog signal where the magnitude of the signal is sampled regularly at uniform intervals, then quantized to a series of symbols in a numeric (usually binary) code. PCM is standard form for digital audio in computers and the compact disc "red book" format.

Upon the participant blowing directly into the breathalyzer hole 166 of the breathalyzer or multi-testing device 118 (also referred to as "real time blow"), the PCM signature of this real time blow is then compared to the PCM signatures of the previously stored acceptable blow sounds and unacceptable blow sounds. In the preferred embodiment, the comparison of the PCM signature of the this real time blow to the PCM signatures of the previously stored acceptable blow sounds and unacceptable blow sounds is accomplished using the statistical outlier test (i.e., Grubbs' test, Dixon's Q test, or any other outlier test known to one skilled in the art) to determine the probability that the PCM signature of the this real time blow matches one of the PCM signatures of the previously stored acceptable blow sounds and unacceptable blow sounds. If the real time blow does not statistically match one of the previously stored acceptable blow sounds and/or does match one of the unacceptable blow sounds, the participant is instructed to repeat the pH validation process again. If the real time blow continues to not match one of the previously stored acceptable blow sounds and/or does match one of the unacceptable blow sounds during the second attempt or again on the third attempt, the participant has failed to provide an acceptable blow to continue the testing process, proceed to Step 117. If the real time blow matches one of the previously stored acceptable blow sounds, the participant has provided an acceptable blow to continue the testing process. Once this is passed, proceed to Step 115.

In an alternative embodiment for determining whether the blow from the participant is acceptable or not acceptable to continue the testing process and again reliably determine when the participant is blowing into the breathalyzer or multi-testing device 118 and, not just giving the appearance of blowing, the microphone 164 could be calibrated. There are 3 steps to calibration.

Step 1:

Ambient sound levels are measured. The person calibrating is requested to count into the microphone 164 during this measurement. The PCM values returned by the way in routines are used to calculate: (i) ambient RMS (root mean square or square root of the arithmetic mean of the squares of the values), (ii) SD (standard deviation), and (iii) Mean. The PCM represents pulse-code modulation, a digital representation of an analog signal where the magnitude of the signal is sampled regularly at uniform intervals, then quantized to a series of symbols in a numeric (usually binary) code. PCM is standard form for digital audio in computers and the compact disc "red book" format.

Step 2:

Blow sound levels are measured. The person calibrating is request to blow a single gentle breath into the microphone. The PCM values are used to calculate: (i) Blow RMS, (ii) Blow SD, (iii) Blow Mean, and (iv) Delta. This is 75% of the value determined by subtracting the Ambient RMS from the Blow RMS.

Step 3:

For the calibration to be acceptable, the absolute value of the Blow SD minus the Ambient SD but be greater than 1 and less than 5. Values less than one would trigger with too little air flow and values greater than 5 would require a very heavy blow to trigger the passive test. To determine that the participant is blowing on each way buffer as it is input, the following values are calculated: (i) RMS, (ii) SD, (iii) Mean, (iv) Sigma. This is the absolute value of the quantity Mean—Blow Mean divided by the Blow SD.

To test then to determine whether the blow from the participant is acceptable or not acceptable to continue the testing process applies the following certain rules or criteria which has two parts. Both tests must be passed for the participant to have provided an acceptable blow to continue the testing process.

Part 1:

This part reduces the likelihood that a finger tap on the microphone will be considered a blow.

Sigma>0.1

Part 2:

This part detects blow like sound.

Sample RMS–Blow RMS>Delta

If the real time blow of the participant is acceptable and/or valid, the system continues with the testing process of the participant as described in Step 115. When the test is completed and the participant has either successfully passed the test or failed the test, the notification of the test results are sent to all the interested persons in the same manner as described in Step 117. In the preferred embodiment for the drug testing kiosk device 102, if the participant successfully passed the test, the passive pass email, as illustrated in FIG. 41, will be sent. If the participant was unsuccessful or failed the test, the passive failed email, as illustrated in FIG. 42, will be sent. Additionally, the drug testing kiosk device 102 provides a written test result to the participant by printing out and providing the written test receipt through the printer receipt report outlet 162 (see FIG. 2).

Thus, there has been provided a unique automated system and method for passive testing of individuals at risk for alcohol and drug abuse. While the invention has been described in conjunction with a specific embodiment, it is evident that many alternatives, modifications and variations will be apparent to those skilled in the art in light of the foregoing description. Accordingly, it is intended to embrace all such alternatives, modifications and variations as fall within the spirit and scope of the appended claims.

What is claimed is:

1. A computer based method for determining if a participant should be tested for alcohol or drugs, comprising the steps of:
   (a) conducting an enrollment of the participant into a computer device comprising the following steps:
      (i) collecting a fingerprint biometric enrollment data of the participant;
      (ii) collecting a voice biometric enrollment data of the participant;
      (iii) collecting an image biometric enrollment data of the participant;
      (iv) creating a testing schedule for the participant, the testing schedule defining a plurality of testing times that the participant is to be tested;
   (b) testing the participant comprising the following steps:
      (i) validating the participant comprising the following steps:
         (1) collecting a fingerprint biometric testing data of the participant;
         (2) comparing the fingerprint biometric testing data to the fingerprint biometric enrollment data to make a determination that the participant testing is the same as the enrollment of the participant;
         (3) collecting a first image biometric testing data of the participant, the first image biometric testing data being collected at substantially the same time as the fingerprint biometric testing data is collected;
         (4) collecting a voice biometric testing data of the participant;
         (5) comparing the voice biometric testing data to the voice biometric enrollment data to make a determination that the participant testing is the same as the enrollment of the participant;
         (6) collecting a second image biometric testing data of the participant, the second image biometric testing data being collected at substantially the same time as the voice biometric testing data is collected;
         (7) collecting a third image biometric testing data of the participant;
         (8) comparing each of the first image biometric testing data, the second image biometric testing data, and the third image biometric testing data to the image biometric enrollment data to make a determination that the participant testing is the same as the enrollment of the participant;
  (ii) performing a test of the participant comprising the following steps:
    (1) blowing of the participant into the computer device for creating testing data of the participant, the third image biometric testing data of the participant being collected at substantially the same time as the blowing of the participant into the computer device for creating testing data of the participant is occurring;
(c) analyzing the testing data of the participant comprising the following steps:
  (i) defining a plurality of tests to compare to the testing data, each of the plurality of tests having assigned to it a test value;
  (ii) comparing the testing data to the test value of each of the plurality of tests and obtaining an individual test result for each of the plurality of tests;
  (iii) defining a plurality of criteria to compare to the individual test results for each of the plurality of tests;
  (iv) applying the individual test results for each of the plurality of tests to the plurality of criteria to make a final determination of the results of the test; and
(d) providing notification of the final determination of the results of the test.

2. The method of claim 1 and further comprising the step of conducting the enrollment of the participant into the computer device by collecting a plurality of personal information of the participant.

3. The method of claim 1 and further comprising the step of conducting the enrollment of the participant into the computer device by collecting medication data of the participant.

4. The method of claim 1 and further comprising the step of selecting the plurality of testing times that the participant is to be tested from the group consisting of Monday, Tuesday, Wednesday, Thursday, Friday, Saturday, and Sunday, each defining a testing day of the week.

5. The method of claim 4 and further comprising the step of selecting the plurality of testing times that the participant is to be tested from any time during a twenty-four hour period of any testing day of the week.

6. The method of claim 1 and further comprising the step of providing that the enrollment of the participant into the computer device further includes collecting a volatile organic compound biometric enrollment data and a pH biometric enrollment data of the participant, each of the volatile organic compound biometric enrollment data and the pH biometric enrollment data being obtained from the blowing of the participant into the computer device.

7. The method of claim 6 and further comprising the step of providing that validating the participant further includes collecting a volatile organic compound biometric testing data, and a pH biometric testing data of the participant.

8. The method of claim 7 and further comprising the step of providing that the volatile organic compound biometric enrollment data is compared to the volatile organic compound biometric testing data, and the pH biometric enrollment data is compared to the pH biometric testing data.

9. The method of claim 8 and further comprising the step of providing that the test of the participant continues if the comparison of the volatile organic compound biometric enrollment data is substantially the same as the volatile organic compound biometric testing data and the pH biometric enrollment data is substantially the same as the pH biometric testing data.

10. The method of claim 1 and further comprising the step of providing that the blowing of the participant is through a straw into the computer device.

11. The method of claim 10 and further comprising the step of conducting a contamination test of the straw if the final determination of the results of the test is a failure.

12. The method of claim 11 and further comprising the step of requesting the participant to provide a replacement straw if the contamination test of the straw is a failure.

13. The method of claim 1 and further comprising the step of providing that the blowing of the participant is directly into the computer device.

14. The method of claim 13 and further comprising the step of conducting a blow test to determine if the blowing of the participant into the computer device is acceptable.

15. The method of claim 6 and further comprising the step of providing that the plurality of tests is selected from the group consisting of blood alcohol content test, volatile organic compound test, and pH test.

16. The method of claim 15 and further comprising the step of providing that the test value of blood alcohol content test is zero.

17. The method of claim 16 and further comprising the step of providing that the test value of the volatile organic compound test is substantially equal to the volatile organic compound biometric enrollment data.

18. The method of claim 17 and further comprising the step of providing that the test value of the pH test is substantially equal to the pH biometric enrollment data.

19. The method of claim 18 and further comprising the step of providing that the testing data is selected from the group consisting of blood alcohol content testing data, volatile organic compound testing data, and pH testing data.

20. The method of claim 19 and further comprising the step of selecting the individual test result for each of the plurality of tests from the group consisting of pass and fail.

21. The method of claim 20 and further comprising the step of providing that the individual test result of the blood alcohol content test is a pass if the blood alcohol content testing data is equal to zero.

22. The method of claim 20 and further comprising the step of providing that the individual test result of the blood alcohol content test is a fail if the blood alcohol content testing data is greater than zero.

23. The method of claim 20 and further comprising the step of providing that the individual test result of the volatile organic compound test is a pass if the volatile organic compound testing data is equal to or less than the volatile organic compound biometric enrollment data.

24. The method of claim 20 and further comprising the step of providing that the individual test result of the volatile organic compound test is a fail if the volatile organic compound testing data is greater than the volatile organic compound biometric enrollment data.

25. The method of claim 20 and further comprising the step of providing that the individual test result of the pH test is a pass if the pH testing data is equal to or less than the pH biometric enrollment data.

26. The method of claim 20 and further comprising the step of providing that the individual test result of the pH is a fail if the pH testing data is greater than the pH biometric enrollment data.

27. The method of claim 20 and further comprising the step of making the final determination of the results of the test a pass if each of the individual test results for each of the plurality of tests is a pass.

28. The method of claim 20 and further comprising the step of making the final determination of the results of the test a pass if the individual test result for blood alcohol content test is a pass, the volatile organic compound test is a pass, and the pH test is a fail.

29. The method of claim 20 and further comprising the step of making the final determination of the results of the test a fail if each of the individual test results for each of the plurality of tests is a fail.

30. The method of claim 20 and further comprising the step of making the final determination of the results of the test a fail if the blood alcohol content test is a fail.

31. The method of claim 20 and further comprising the step of making the final determination of the results of the test a fail if the blood alcohol content test is a pass, the volatile organic compound test is a fail, and the pH test is a pass.

32. The method of claim 20 and further comprising the step of making the final determination of the results of the test a fail if the blood alcohol content test is a pass, the volatile organic compound test is a fail, and the pH test is a fail.

33. A computer based method for determining if a participant should be tested for alcohol or drugs, comprising the steps of:
   (a) conducting an enrollment of the participant into a computer device comprising the following steps:
      (i) collecting a fingerprint biometric enrollment data of the participant;
      (ii) collecting a voice biometric enrollment data of the participant;
      (iii) collecting an image biometric enrollment data of the participant;
   (b) testing the participant comprising the following steps:
      (i) validating the participant comprising the following steps:
         (1) collecting a fingerprint biometric testing data of the participant;
         (2) comparing the fingerprint biometric testing data to the fingerprint biometric enrollment data to make a determination that the participant testing is the same as the enrollment of the participant;
         (3) collecting a first image biometric testing data of the participant, the first image biometric testing data being collected at substantially the same time as the fingerprint biometric testing data is collected;
         (4) collecting a voice biometric testing data of the participant;
         (5) comparing the voice biometric testing data to the voice biometric enrollment data to make a determination that the participant testing is the same as the enrollment of the participant;
         (6) collecting a second image biometric testing data of the participant, the second image biometric testing data being collected at substantially the same time as the voice biometric testing data is collected;
         (7) collecting a third image biometric testing data of the participant;
         (8) comparing each of the first image biometric testing data, the second image biometric testing data, and the third image biometric testing data to the image biometric enrollment data to make a determination that the participant testing is the same as the enrollment of the participant;
      (ii) performing a test of the participant comprising the following steps:
         (1) blowing of the participant into the computer device for creating testing data of the participant, the third image biometric testing data of the participant being collected at substantially the same time as the blowing of the participant into the computer device for creating testing data of the participant is occurring;
   (c) analyzing the testing data of the participant; and
   (d) providing notification of the final determination of the results of the test.

* * * * *